United States Patent
Lupia et al.

(10) Patent No.: US 7,678,381 B2
(45) Date of Patent: Mar. 16, 2010

(54) STABILIZED BODY CARE PRODUCTS, HOUSEHOLD PRODUCTS, TEXTILES AND FABRICS

(75) Inventors: Joseph Anthony Lupia, Reinach (CH); Oliver Reich, Grenzach-Wyhlen (DE); Karla Wilzer, Greensboro, NC (US)

(73) Assignee: Ciba Specialty Chemicals Corporation, Tarytown, NY (US)

( * ) Notice: Subject to any disclaimer, the term of this patent is extended or adjusted under 35 U.S.C. 154(b) by 946 days.

(21) Appl. No.: 10/576,915

(22) PCT Filed: Oct. 25, 2004

(86) PCT No.: PCT/EP2004/052644
§ 371 (c)(1),
(2), (4) Date: Apr. 24, 2006

(87) PCT Pub. No.: WO2005/042828
PCT Pub. Date: May 12, 2005

(65) Prior Publication Data
US 2007/0079446 A1    Apr. 12, 2007

(30) Foreign Application Priority Data
Nov. 3, 2003   (EP)   ................... 03104057

(51) Int. Cl.
A61Q 1/00    (2006.01)
C11D 7/26    (2006.01)
C11D 7/32    (2006.01)
C11D 7/40    (2006.01)

(52) U.S. Cl. .......................... 424/401; 424/49; 424/65; 424/69; 424/70.1; 510/119; 510/130; 510/137; 510/276; 510/499; 510/500

(58) Field of Classification Search ................ 510/119, 510/130, 137, 276, 499, 500; 8/405; 424/49, 424/65, 69, 70.1, 401
See application file for complete search history.

(56) References Cited

U.S. PATENT DOCUMENTS

| | | | |
|---|---|---|---|
| 6,254,724 B1 * | 7/2001 | Seltzer et al. | 162/70 |
| 6,599,326 B1 | 7/2003 | Seltzer et al. | 8/101 |
| 6,630,002 B2 | 10/2003 | Koller et al. | 8/402 |
| 2002/0088574 A1 | 7/2002 | Seltzer et al. | 162/72 |
| 2004/0023837 A1 * | 2/2004 | Zanardi et al. | 510/499 |
| 2006/0040836 A1 | 2/2006 | Lupia et al. | 510/130 |
| 2006/0051478 A1 | 3/2006 | Seltzer et al. | 426/531 |

FOREIGN PATENT DOCUMENTS

| | | | |
|---|---|---|---|
| WO | 96/15110 | | 5/1996 |
| WO | 01/07550 | | 2/2001 |
| WO | WO01/36396 | * | 5/2001 |
| WO | 03/103622 | | 12/2003 |
| WO | WO2004/076419 | * | 9/2004 |

* cited by examiner

Primary Examiner—Gregory R Del Cotto
(74) Attorney, Agent, or Firm—Mervin G. Wood

(57) ABSTRACT

Disclosed are stabilized body care products, household products, textiles and fabrics comprising an effective stabilizing amount of at least one compound selected from the group consisting of formula (I)-(III)

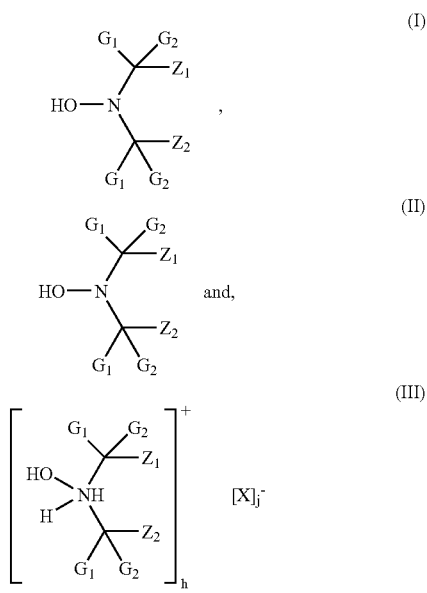

where
$G_1$ and $G_2$ are independently alkyl of 1 to 4 carbon atoms or are together pentamethylene,
$Z_1$ and $Z_2$ are each methyl, or $Z_1$ and $Z_2$ together form a linking moiety which may additionally be substituted by an ester, ether, hydroxy, oxo, cyanohydrin, amide, amino, carboxy or urethane group,
X is an inorganic or organic anion, and
where the total charge of cations h is equal to the total charge of anions j; and an organic UV filter selected from
($c_1$) dibenzoylmethane derivatives;
($c_2$) cinnamic acid esters;
($c_3$) camphor derivatives; and
($c_4$) trianilino-s-triazine derivatives.

10 Claims, No Drawings

STABILIZED BODY CARE PRODUCTS, HOUSEHOLD PRODUCTS, TEXTILES AND FABRICS

The present invention relates to the use of selected hindered nitroxyl, hydroxylamine and hydroxylamine salt compounds and selected organic UV filters for the protection of body care products, personal care products, household products, fabric care products, institutional & industrial products, textiles and fabrics against the deleterious effects of light, heat and oxygen.

Since consumers today can choose from a large variety of Home & Personal Care products, producers need to communicate clearly how their brands are unique. Sophisticated products containing new fragrances and actives in many colorful formulations, displayed in transparent and translucent packaging are today very common.

It is mandatory for commercial success that the pleasant appearance, product efficacy and the fresh smell of a consumer product will last during its whole product life cycle even when exposed heavily to UV-light. This exposure can result in decomposition processes and strong color fading destroying the product appearance, active ingredients and fragrance.

Various stabilization techniques of clear package products by absorption of UV light are commonly used and well known. For example broad-band UV light stabilizers of the benzotriazole class enhance product's stability and shelf live due to their very good UV-A and UV-B absorption properties, compared to other absorbers such as benzophenones where mainly UV-B light is absorbed.

However, by just the absorption of UV light, not all potential degradation pathways are blocked.

Surprisingly it was found that an effective protection can be achieved with specific compounds selected from nitroxyl compounds, hindered hydroxylamine compounds and hindered hydroxylamine salt compounds and specific organic UV absorbers.

BACKGROUND

WO 01/07550 teaches the treatment of fabric with hindered amine stabilizers.

U.S. Pat. No. 6,254,724 teaches the stabilization of pulp and paper with hindered-amine based compounds.

DETAILED DISCLOSURE

The present invention pertains to a stabilized composition comprising
(a) a body care product, household product, textile or fabric and
(b) an effective stabilizing amount of at least one compound selected from the group consisting of
  (i) hindered nitroxyl compounds of formula (I)

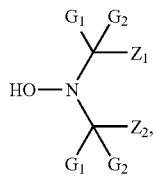

(ii) hindered hydroxylamine compounds of formula (II)

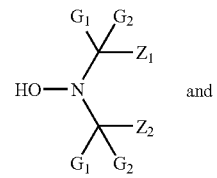

(iii) hindered hydroxylamine salt compounds of formula (III)

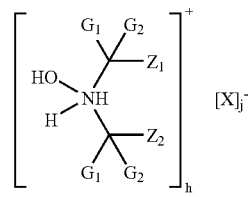

where
$G_1$ and $G_2$ are independently alkyl of 1 to 4 carbon atoms or are together pentamethylene,
$Z_1$ and $Z_2$ are each methyl, or $Z_1$ and $Z_2$ together form a linking moiety which may additionally be substituted by an ester, ether, hydroxy, oxo, cyanohydrin, amide, amino, carboxy or urethane group,
X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and where the total charge of cations h is equal to the total charge of anions j: and
(c) an organic UV filter selected from
  ($c_1$) dibenzoylmethane derivatives;
  ($c_2$) cinnamic acid esters;
  ($c_3$) camphor derivatives; and
  ($c_4$) trianilino-s-triazine derivatives.

For instance, X is chloride, bisulfite, bisulfate, sulfate, phosphate, nitrate, ascorbate, acetate, citrate or carboxylate of ethylenediaminetetraacetic acid or of diethylenetriaminepentaacetic acid; for instance X is bisulfate or citrate.

The hindered nitroxyl, hydroxylamine and hydroxylamine salt compounds of component (b) are for example of formulae A to EE and A* to EE*

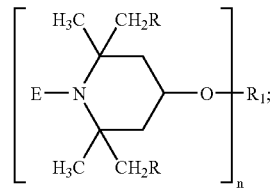

(A)

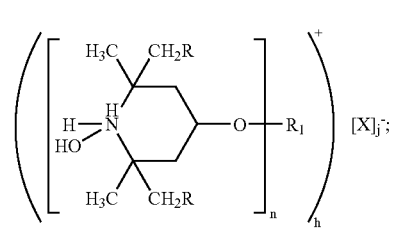 (A*)
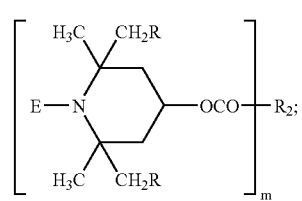 (B)
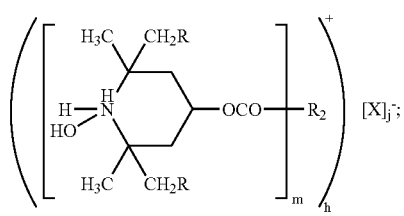 (B*)
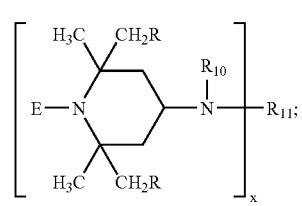 (C)
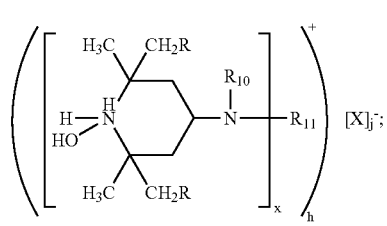 (C*)
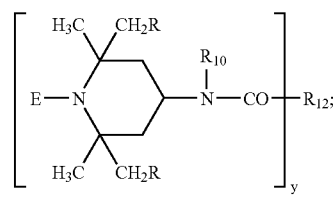 (D)
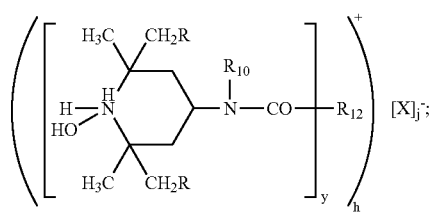 (D*)
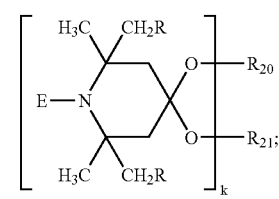 (E)
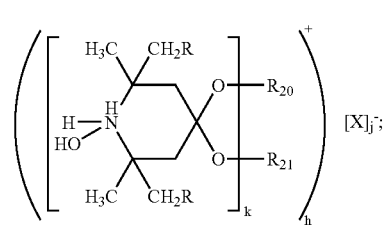 (E*)
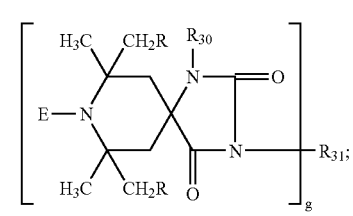 (F)
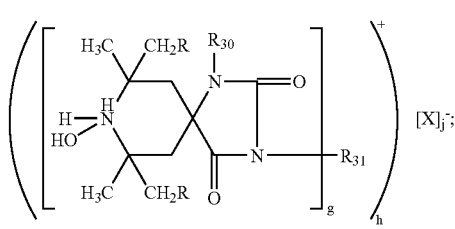 (F*)
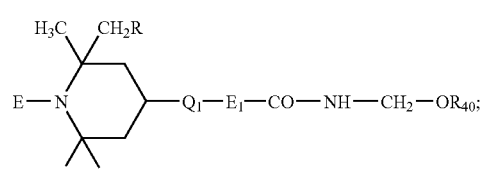 (G)
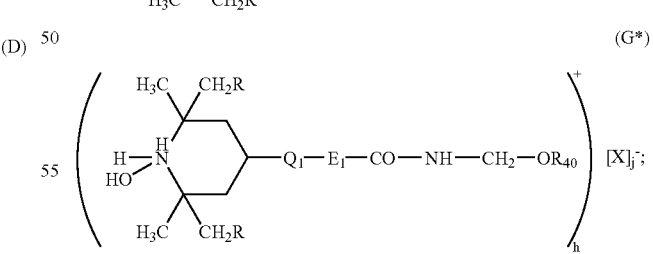 (G*)
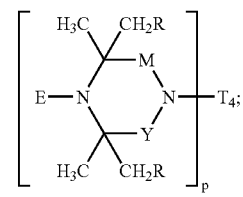 (H)

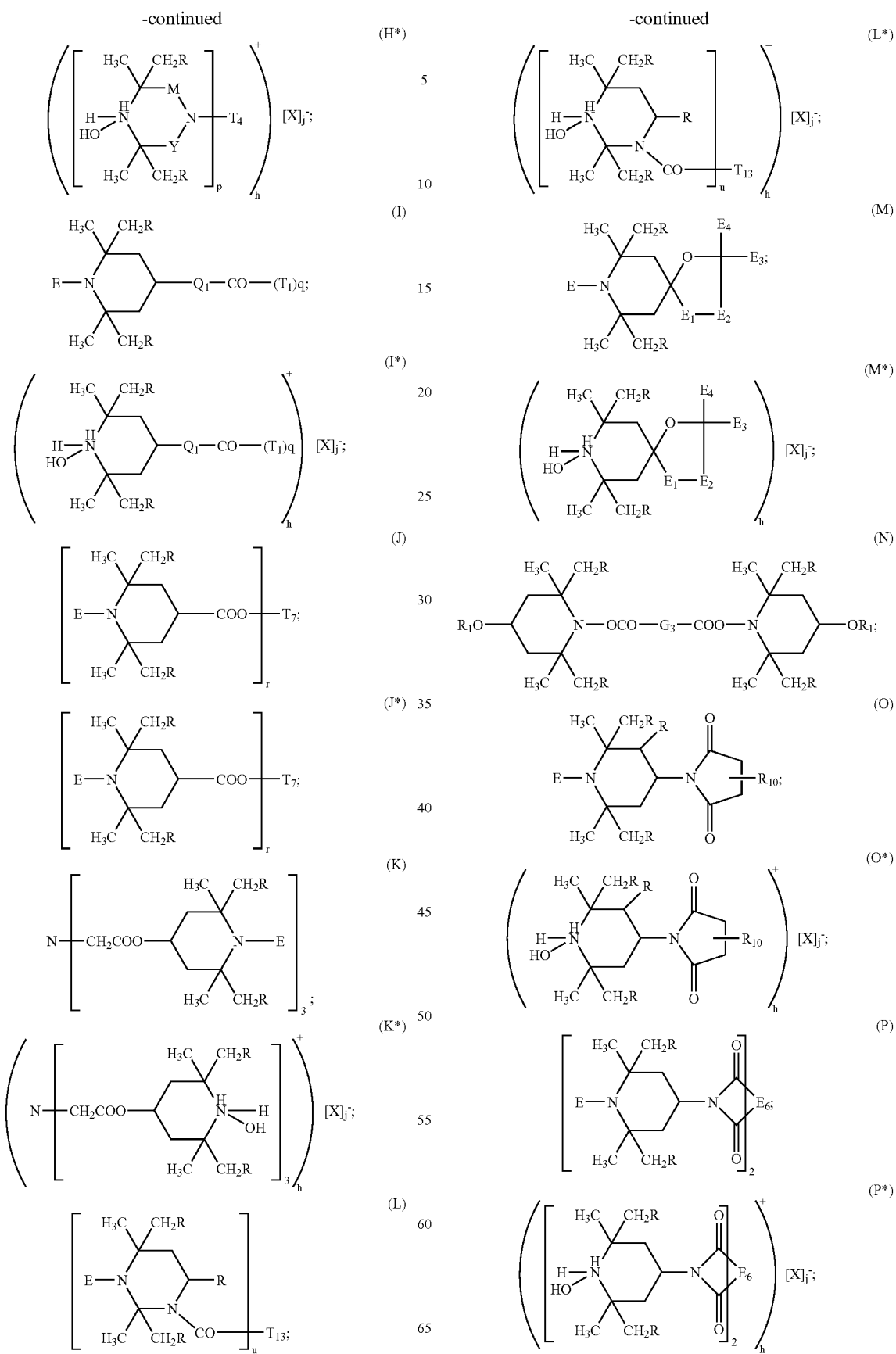

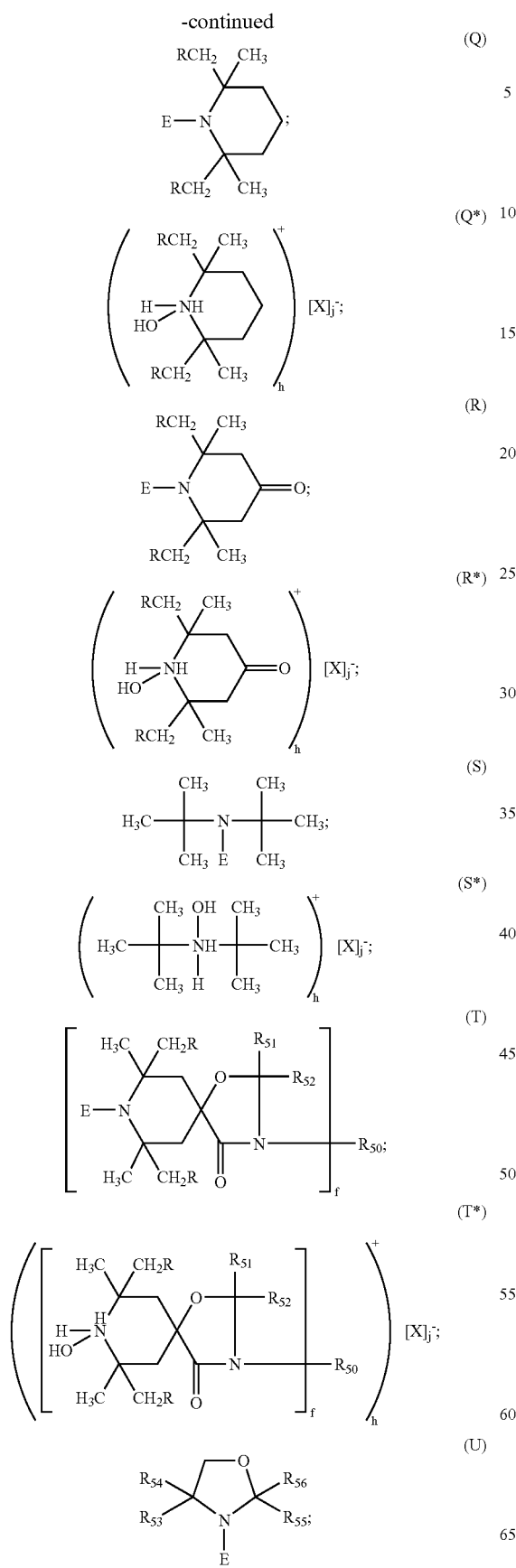
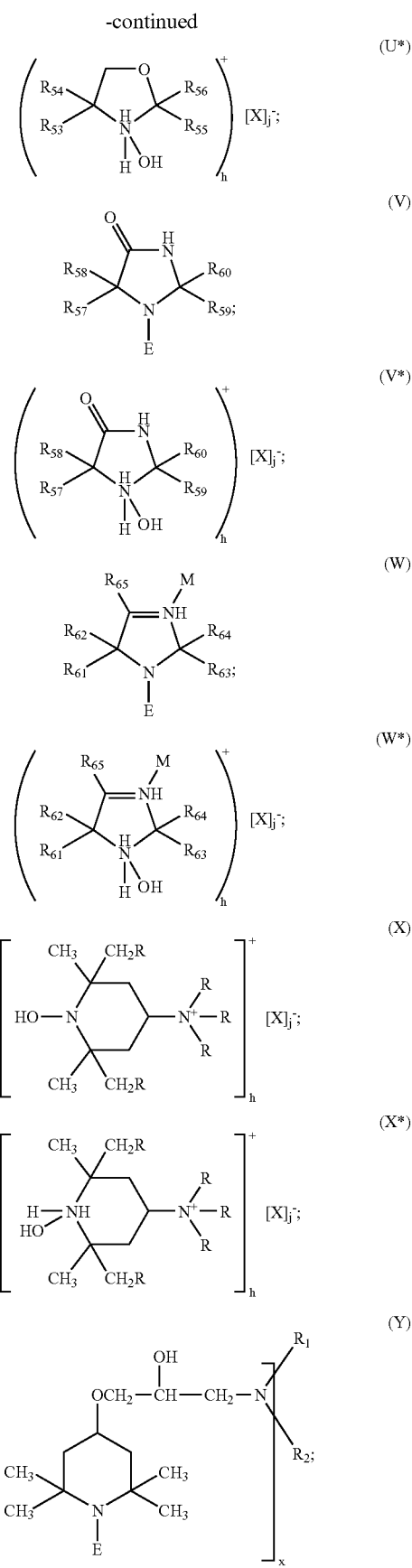

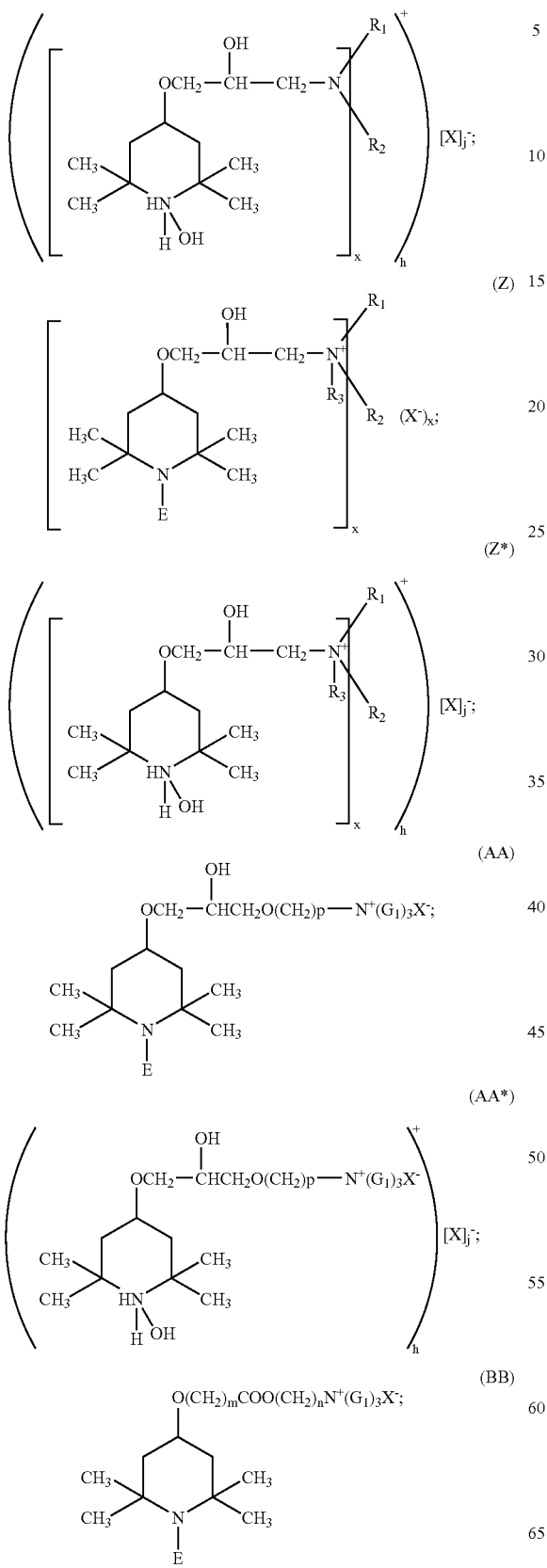
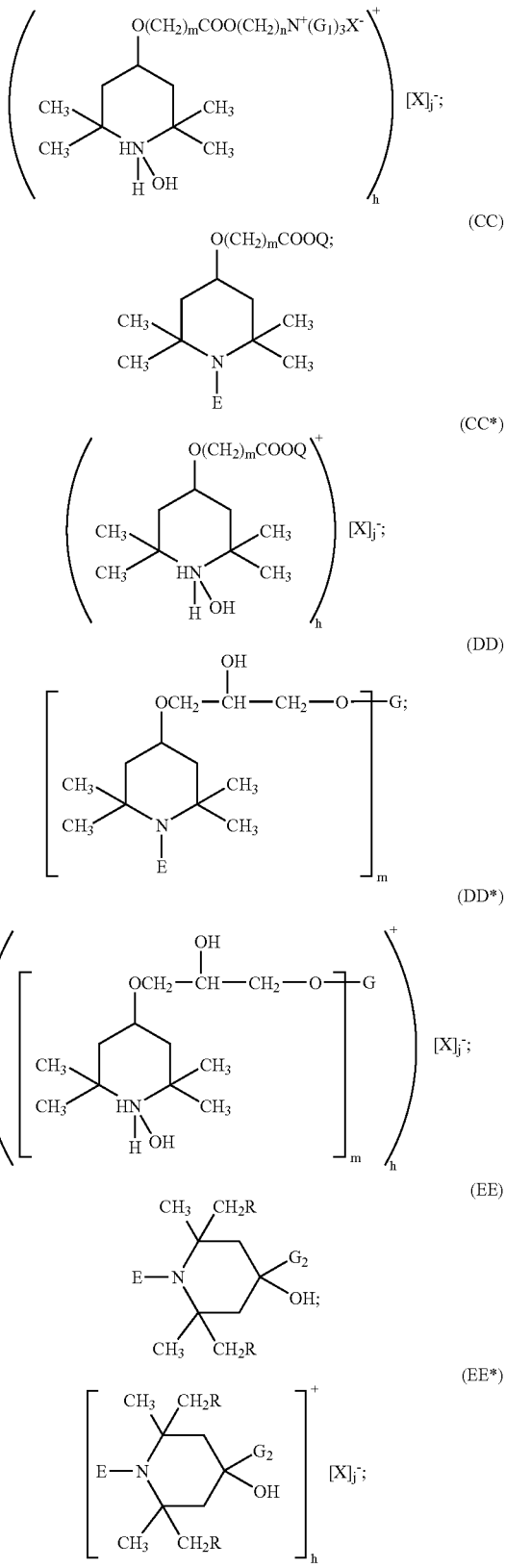

wherein

E is oxyl or hydroxyl,

R is hydrogen or methyl, in formula A and A*, n is 1 or 2, when n is 1, $R_1$ is hydrogen, alkyl of 1 to 18 carbon atoms, alkenyl of 2-18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N$^{n+}$(R$_2$)$_4$ where $R_2$ is alkyl of 1 to 8 carbon atoms or benzyl, when n is 2, $R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula B and B*, m is 1 to 4, when m is 1, $R_2$ is alkyl of 1 to 18 carbon atoms, alkyl of 3 to 18 carbon atoms interrupted by —COO—, or $R_2$ is —CH$_2$(OCH$_2$CH$_2$)$_n$OCH$_3$ where n is 1 to 12, or $R_2$ is cycloalkyl of 5 to 12 carbon atoms, aryl of 6 to 12 carbon atoms, or said aryl substituted by one to four alkyl groups of 1 to 4 carbon atoms, or $R_2$ is —NHR$_3$ where $R_3$ is alkyl of 1 to 18 carbon atoms, cycloalkyl of 5 to 12 carbon atoms, aryl of 6 to 12 carbon atoms, or said aryl substituted by one to four alkyl of 1 to 4 carbon atoms, or $R_2$ is —N(R$_3$)$_2$ where $R_3$ is as defined above, when m is 2, $R_2$ is alkylene of 1 to 12 carbon atoms, alkenylene of 4 to 12 carbon atoms, xylylene, alkylene of 2 to 12 carbon atoms interrupted by —COO—, or $R_2$ is —CH$_2$(OCH$_2$CH$_2$)$_n$OCH$_2$— where n is 1 to 12, or $R_2$ is cycloalkylene of 5 to 12 carbon atoms, aralkylene of 7 to 15 carbon atoms or arylene of 6 to 12 carbon atoms, or $R_2$ is —NHR$_4$NH— where $R_4$ is alkylene of 2 to 18 carbon atoms, cycloalkylene of 5 to 12 carbon atoms, aralkylene of 8 to 15 carbon atoms or arylene of 6 to 12 carbon atoms, or $R_2$ is —N(R$_3$)R$_4$N(R$_3$)— where $R_3$ and $R_4$ are as defined above, or $R_2$ is —CO— or —NH—CO—NH—, when m is 3, $R_2$ is alkanetriyl of 3 to 8 carbon atoms or benzenetriyl, or when m is 4, $R_2$ is alkanetetrayl of 5 to 8 carbon atoms or benzenetetrayl, in formula C and C*, $R_{10}$ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl, x is 1 or 2, when x is 1, $R_{11}$ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_{11}$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N$^{n+}$(R$_2$)$_4$ where $R_2$ is hydrogen, alkyl of 1 to 8 carbon atoms or benzyl, or when x is 2, $R_{11}$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula D and D*, $R_{10}$ is as defined above, y is 1 to 4, and $R_{12}$ is defined as $R_2$ above in formula E and E*, k is 1 or 2, when k is 1, $R_{20}$ and $R_{21}$ are independently alkyl of 1 to 12 carbon atoms, alkenyl of 2 to 12 carbon atoms or aralkyl of 7 to 15 carbon atoms, or $R_{20}$ is also hydrogen, or $R_{20}$ and $R_{21}$ together are alkylene of 2 to 8 carbon atoms or said alkylene substituted by hydroxyl, or are acyloxy-alkylene of 4 to 22 carbon atoms, or when k is 2, $R_{20}$ and $R_{21}$ are together (—CH$_2$)$_2$C(CH$_2$—)$_2$, in formula F and F*, $R_{30}$ is hydrogen, alkyl of 1 to 18 carbon atoms, benzyl, glycidyl, or alkoxyalkyl of 2 to 6 carbon atoms, g is 1 or 2, when g is 1, $R_{31}$ is defined as $R_1$ above when n is 1, when g is 2, $R_{31}$ is defined as $R_1$ above when n is 2, in formula G and G*, $Q_1$ is —NR$_{41}$— or —O—, $E_1$ is alkylene of 1 to 3 carbon atoms, or $E_1$ is —CH$_2$—CH(R$_{42}$)—O— where $R_{42}$ is hydrogen, methyl or phenyl, or $E_1$ is —(CH$_2$)$_3$—NH— or $E_1$ is a direct bond, $R_{40}$ is hydrogen or alkyl of 1 to 18 carbon atoms, $R_{41}$ is hydrogen, alkyl of 1 to 18 carbon atoms, cycloalkyl of 5 to 12 carbon atoms, aralkyl of 7 to 15 carbon atoms, aryl of 6 to 10 carbon atoms, or $R_{41}$ is —CH$_2$—CH(R$_{42}$)—OH where $R_{42}$ is as defined above, in formula H and H*, p is 1 or 2, $T_4$ is as defined for $R_{11}$ when x is 1 or 2, M and Y are independently methylene or carbonyl, for instance M is methylene and Y is carbonyl, in formula I and I*, this formula denotes a recurring structural unit of a polymer where $T_1$ is ethylene or 1,2-propylene or is the repeating structural unit derived from an alpha-olefin copolymer with an alkyl acrylate or methacrylate, and where q is 2 to 100, $Q_1$ is —N(R$_{41}$)— or —O— where $R_{41}$ is as defined above, in formula J and J*, r is 1 or 2, $T_7$ is as defined for $R_1$ when n is 1 or 2 in formula A, for example $T_7$ is octamethylene when r is 2, in formula L and L*, u is 1 or 2, $T_{13}$ is as defined for $R_1$ when n is 1 or 2 in formula A, with the proviso that $T_{13}$ is not hydrogen when u is 1, in formula M and M*, $E_1$ and $E_2$, being different, each are —CO— or —N($E_5$)- where $E_5$ is hydrogen, alkyl of 1 to 12 carbon atoms or alkoxycarbonylalkyl of 4 to 22 carbon atoms, for instance $E_1$ is —CO— and $E_2$ is —N($E_5$)-, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by one to four alkyl of 1 to 4 carbon atoms, for example methyl, in formula N, $R_1$ is as defined for $R_1$ in formula A when n is 1, $G_3$ is a direct bond, alkylene of 1 to 12 carbon atoms, phenylene or —NH-$G_1$-NH— where $G_1$ is alkylene of 1 to 12 carbon atoms, in formula O and O*, $R_{10}$ is as defined for $R_{10}$ in formula C, in formula P and P*, $E_6$ is an aliphtic or aromatic tetravalent radical, for example neopentanetetrayl or benzenetetrayl, in formula T and T*, $R_{51}$ is hydrogen, alkyl of 1 to 18 carbon atoms, cycloalkyl of 5 to 12 carbon atoms, or aryl of 6 to 10 carbon atoms, $R_{52}$ is hydrogen or alkyl of 1 to 18 carbon atoms, or $R_{51}$ and $R_{52}$ together of alkylene of 4 to 8 carbon atoms, f is 1 or 2, when f is 1, $R_{50}$ is as defined for $R_{11}$ in formula C when x is 1, or $R_{50}$ is —$(CH_2)_z COOR_{54}$ where z is 1 to 4 and $R_{54}$ is hydrogen or alkyl of 1 to 18 carbon atoms, or $R_{54}$ a metal ion from the 1st, 2nd or 3rd group of the periodic table or a group —$N(R_{55})_4$ where $R_{55}$ is hydrogen, alkyl of 1 to 12 carbon atoms or benzyl, when f is 2, $R_{50}$ is as defined for $R_{11}$ in formula C when x is 2, in formula U and U*, $R_{53}$, $R_{54}$, $R_{55}$ and $R_{56}$ are independently alkyl of 1 to 4 carbon atoms or are together pentamethylene.

in formula V and V*, $R_{57}$, $R_{58}$, $R_{59}$ and $R_{60}$ are independently alkyl of 1 to 4 carbon atoms or are together pentamethylene.

in formula W and W*, $R_{61}$, $R_{62}$, $R_{63}$ and $R_{64}$ are independently alkyl of 1 to 4 carbon atoms or are together pentamethylene, $R_{65}$ is alkyl of 1 to 5 carbon atoms, M is hydrogen or oxygen, wherein in formulas X to CC and X* to CC* n is 2 to 3, $G_1$ is hydrogen, methyl, ethyl, butyl or benzyl, m is 1 to 4, x is 1 to 4, when x is 1, $R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen, or $R_1$ and $R_2$ are together tetramethylene, pentamethylene, hexamethylene or 3-oxapentamethylene, when x is 2, $R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group, $R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups; o-, m- or p-phenylene or said phenylene substituted by one or two alkyl of 1 to 4 carbon atoms, or $R_2$ is —$(CH_2)_k O[(CH_2)_k O]_h (CH_2)_k$— where k is 2 to 4 and h is 1 to 40, or $R_1$ and $R_2$ together with the two N atoms to which they are attached are piperazin-1,4-diyl, when x is 3, $R_1$ is hydrogen $R_2$ is alkylene of 4 to 8 carbon atoms interrupted by one nitrogen atom, when x is 4, $R_1$ is hydrogen, $R_2$ is alkylene of 6 to 12 carbon atoms interrupted by two nitrogen atoms, $R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group, P is 2 or 3, and Q is an alkali metal salt, ammonium or $N^+(G_1)_4$, in formula DD and DD* m is 2 or 3, when m is 2,

G is —$(CH_2CHR—O)_r CH_2CHR$—, where r is 0 to 3, and R is hydrogen or methyl, and when m is 3, G is glyceryl, in formula EE and EE*

$G_2$ is —CN, —$CONH_2$ or —$COOG_3$ where $G_3$ is hydrogen, alkyl of 1 to 18 carbon atoms or phenyl, X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and where the total charge of cations h is equal to the total charge of anions j.

For example, the compounds of component (b) are those of formulas A, A*, B, B*, C, C*, D, D*, Q, Q*, R, R*, S, S*, X, X*, Y, *Y, Z and Z*, R is hydrogen, in formula A and A* n is 1 or 2, when n is 1, $R_1$ is hydrogen, alkyl of 1 to 6 carbon atoms, alkenyl of 2-6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or R₁ is alkyl of 1 to 4 carbon atoms substituted by a carboxy group or by —COOZ where Z is hydrogen or alkyl of 1 to 4 carbon atoms,
when n is 2,
R₁ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups,
in formula B and B*
m is 1 or 2
when m is 1,
R₂ is alkyl of 1 to 4 carbon atoms or R₂ is CH₂(OCH₂CH₂)ₙOCH₃ where n is 1 to 12, or
R₂ is phenyl, or said phenyl substituted by one to three methyl groups,
R₂ is —NHR₃ where R₃ is alkyl of 1 to 4 carbon atoms or phenyl, or said phenyl substituted by one or two methyl groups,
when m is 2,
R₂ is alkylene of 1 to 8 carbon atoms, alkenylene of 4 to 8 carbon atoms, or R₂ is —CH₂(OCH₂CH₂)ₙOCH₂— where n is 1 to 12,
R₂ is NHR₄NH where R₄ is of 2 to 6 carbon atoms, aralkylene of 8 to 15 carbon atoms or arylene of 6 to 12 carbon atoms,
R₂ is —CO— or —NHCONH,
in formula C and C*,
R₁₀ is hydrogen or, alkanoyl of 1 to 3 carbon atoms,
x is 1 or 2,
when x is 1,
R₁₁ is hydrogen, alkyl of 1 to 6 carbon atoms or glycidyl,
R₁₁ is allyl of 1 to 4 carbon atoms substituted by a carboxy group or by COOZ where Z is hydrogen or alkyl of 1 to 4 carbon atoms,
when x is 2,
R₁₁ is alkylene of 1 to 6 carbon atoms,
in formula D and D*,
R₁₀ is hydrogen,
y is 1 or 2,
R₁₂ is defined as R₂ above,
in formula Y, Y*, Z and Z*,
x is 1 or 2,
when x is 1,
R₁ and R₂ are independently alkyl of 1 to 4 carbon atoms, or R₁ and R₂ are together tetramethylene, or pentamethylene,
R₂ is hydrogen or alkyl of 1 to 4 carbon atoms, said alkyl group substituted by a hydroxyl group,
when x is 2,
R₁ is hydrogen, alkyl of 1 to 4 carbon atoms, said alkyl substituted by a hydroxyl group,
R₂ is alkylene of 2 to 6 carbon atoms,
R₃ is as defined above.

For instance, the compounds of component (b) are those of formulas A, A*, B, B*, C, C*, D, D*, Q, Q*, R and R*,
R is hydrogen,
in formula A and A*,
h is 1,
R₁ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or
R₁ is alkyl of 1 to 4 carbon atoms substituted by —COOZ where Z is hydrogen or alkyl of 1 to 4 carbon atoms,
in formula B and B*,
m is 1 or 2,
R₂ is alkyl of 1 to 4 carbon atoms or R₂ is CH₂(OCH₂CH₂)ₙOCH₃ where n is 1 to 4,
when m is 2,
R₂ is alkylene of 1 to 8 carbon atoms,
in formula C and C*,
R₁₀ is hydrogen or alkanoyl of 1 or 2 carbon atoms,
x is 1 or 2,
when x is 1,
R₁₁ is hydrogen, alkyl of 1 to 4 carbon atoms or glycidyl,
R₁₁ is alkyl of 1 to 4 carbon atoms substituted by COOZ where Z is hydrogen or alkyl of 1 to 4 carbon atoms,
when x is 2,
R₁₁ is alkylene of 1 to 6 carbon atoms,
in formula D and D*,
R₁₀ is hydrogen,
y is 1 or 2,
R₁₂ is defined as R₂ above.

For instance, the hindered nitroxyl, hydroxylamine and hydroxylamine salt compounds of component (b) are selected from bis(1-oxyl-2,2-6-6-tetramethylpiperidin-4-yl)sebacate; bis(1-hydroxy-2,2-6-6-tetramethylpiperidin-4-yl)sebacate; 1-hydroxy-2,2-6-6-tetramethyl-4-acetoxypiperidinium citrate; 1-oxyl-2,2,6,6-tetramethyl-4-acetamidopiperidine; 1-hydroxy-2,2,6,6-tetramethyl-4-acetamidopiperidine; 1-hydroxy-2,2,6,6-tetramethyl-4-acetamidopiperidinium bisulfate; 1-oxyl-2,2,6,6-tetramethyl-4-oxo-piperidine; 1-hydroxy-2,2,6,6-tetramethyl-4-oxo-piperidine; 1-hydroxy-2,2,6,6-tetramethyl-4-oxo-piperidinium acetate; 1-oxyl-2,2,6,6-tetramethyl-4-methoxy-piperidine; 1-hydroxy-2,2,6,6-tetramethyl-4-methoxy-piperidine; 1-hydroxy-2,2,6,6-tetramethyl-4-methoxy-piperidinium acetate; 1-oxyl-2,2,6,6-tetramethyl-4-acetoxypiperidine; 1-hydroxy-2,2,6,6-tetramethyl-4-acetoxypiperidine; 1-oxyl-2,2,6,6-tetramethyl-4-propoxy-piperidine; 1-hydroxy-2,2,6,6-tetramethyl-4-propoxy-piperidinium acetate; 1-hydroxy-2,2,6,6-tetramethyl-4-propoxy-piperidine; 1-oxyl-2,2,6,6-tetramethyl-4-(2-hydroxy-4-oxapentoxy)piperidine; 1-hydroxy-2,2,6,6-tetramethyl-4-(2-hydroxy-4-oxapentoxy)piperidinium acetate; 1-oxyl-2,2,6,6-tetramethyl-4-hydroxypiperidine; 1-hydroxy-2,2,6,6-tetramethyl-4-hydroxypiperidine; 1-hydroxy-2,2,6,6-tetramethyl-4-hydroxypiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium)citrate; tris(1-hydroxy-2,2,6,6-tetramethyl-4-hydroxypiperidinium)citrate; tetra(1-hydroxy-2,2,6,6-tetramethyl-4-hydroxypiperidinium)ethylenediaminetetraacetate; tetra(1-hydroxy-2,2,6,6-tetramethyl-4-acetamidopiperidinium)ethylenediaminetetraacetate; tetra(1-hydroxy-2,2,6,6-tetramethyl-4-oxopiperidinium)ethylenediaminetetraacetate; penta(1-hydroxy-2,2,6,6-tetramethyl-4-hydroxypiperidinium)diethylenetriaminepentaacetate; penta(1-hydroxy-2,2,6,6-tetramethyl-4-acetamidopiperidinium)diethylenetriaminepentaacetate; penta(1-hydroxy-2,2,6,6-tetramethyl-4-oxopiperidinium)diethylenetriaminepentaacetate; tri(1-hydroxy-2,2,6,6-tetramethyl-4-hydroxypiperidinium)nitrilotriacetate; tri(1-hydroxy-2,2,6,6-tetramethyl-4-acetamidopiperidinium)nitrilotriacetate; tri(1-hydroxy-2,2,6,6-tetramethyl-4-oxopiperidinium)nitrilotriacetate; penta(1-hydroxy-2,2,6,6-tetramethyl-4-hydroxypiperidinium)diethylenetriaminepentamethylenephosphonate; penta(1-hydroxy-2,2,6,6-tetramethyl-4-acetamidopiperidinium)

diethylenetriamine-pentamethylenephosphonate; and penta (1-hydroxy-2,2,6,6-tetramethyl-4-oxopiperidinium) diethylenetriaminepentamethylenephosphonate.

For example, the hindered nitroxyl, hydroxylamine and hydroxylamine salt compounds of component (b) are selected from 1-oxyl-2,2,6,6-tetramethyl-4-hydroxypiperidine; 1-hydroxy-2,2,6,6-tetramethyl-4-hydroxypiperidine; 1-hydroxy-2,2,6,6-tetramethyl-4-hydroxypiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium)citrate; tris(1-hydroxy-2,2,6,6-tetramethyl-4-hydroxypiperidinium)citrate; tetra(1-hydroxy-2,2,6,6-tetramethyl-4-hydroxypiperidinium) ethylenediaminetetraacetate; tetra(1-hydroxy-2,2,6,6-tetramethyl-4-acetamidopiperidinium) ethylenediaminetetraacetate; tetra(1-hydroxy-2,2,6,6-tetramethyl-4-oxopiperidinium) ethylenediaminetetraacetate; penta(1-hydroxy-2,2,6,6-tetramethyl-4-hydroxypiperidinium) diethylenetriaminepentaacetate; penta(1-hydroxy-2,2,6,6-tetramethyl-4-acetamidopiperidinium) diethylenetriaminepentaacetate; and penta(1-hydroxy-2,2,6,6-tetramethyl-4-oxopiperidinium) diethylenetriaminepentaacetate.

For example, the compounds of component (b) are selected from 1-hydroxy-2,2,6,6-tetramethyl-4-hydroxypiperidinium citrate; bis(1-hydroxy-2,2,6,6-tetramethyl-4-hydroxypiperidinium)citrate; tris(1-hydroxy-2,2,6,6-tetramethyl-4-hydroxypiperidinium)citrate; 1-hydroxy-2,2,6,6-tetramethyl-4-hydroxypiperidinium DTPA; bis(1-hydroxy-2,2,6,6-tetramethyl-4-hydroxypiperidinium) DTPA; tris(1-hydroxy-2,2,6,6-tetramethyl-4-hydroxypiperidinium) DTPA; tetrakis(1-hydroxy-2,2,6,6-tetramethyl-4-hydroxypiperidinium) DTPA; pentakis(1-hydroxy-2,2,6,6-tetramethyl-4-hydroxypiperidinium) DTPA; 1-hydroxy-2,2,6,6-tetramethyl-4-hydroxypiperidinium EDTA; bis(1-hydroxy-2,2,6,6-tetramethyl-4-hydroxypiperidinium) EDTA; tris(1-hydroxy-2,2,6,6-tetramethyl-4-hydroxypiperidinium) EDTA; tetrakis(1-hydroxy-2,2,6,6-tetramethyl-4-hydroxypiperidinium) EDTA; 1-hydroxy-2,2,6,6-tetramethyl-4-oxo-piperidinium citrate; bis(1-hydroxy-2,2,6,6-tetramethyl-4-oxo-piperidinium)citrate; tris(1-hydroxy-2,2,6,6-tetramethyl-4-oxo-piperidinium)citrate; 1-hydroxy-2,2,6,6-tetramethyl-4-oxo-piperidinium DTPA; bis(1-hydroxy-2,2,6,6-tetramethyl-4-oxo-piperidinium) DTPA; tris(1-hydroxy-2,2,6,6-tetramethyl-4-oxo-piperidinium) DTPA; tetrakis(1-hydroxy-2,2,6,6-tetramethyl-4-oxo-piperidinium) DTPA; pentakis(1-hydroxy-2,2,6,6-tetramethyl-4-oxo-piperidinium) DTPA; 1-hydroxy-2,2,6,6-tetramethyl-4-oxo-piperidinium EDTA; bis(1-hydroxy-2,2,6,6-tetramethyl-4-oxo-piperidinium) EDTA; tris(1-hydroxy-2,2,6,6-tetramethyl-4-oxo-piperidinium) EDTA; tetrakis(1-hydroxy-2,2,6,6-tetramethyl-4-oxo-piperidinium) EDTA; 1-hydroxy-2,2,6,6-tetramethyl-4-acetamidopiperidinium citrate; bis(1-hydroxy-2,2,6,6-tetramethyl-4-acetamidopiperidinium)citrate; tris(1-hydroxy-2,2,6,6-tetramethyl-4-acetamidopiperidinium) citrate; 1-hydroxy-2,2,6,6-tetramethyl-4-acetamidopiperidinium DTPA; bis(1-hydroxy-2,2,6,6-tetramethyl-4-acetamidopiperidinium) DTPA; tris(1-hydroxy-2,2,6,6-tetramethyl-4-acetamidopiperidinium) DTPA; tetrakis(1-hydroxy-2,2,6,6-tetramethyl-4-acetamidopiperidinium) DTPA; pentakis(1-hydroxy-2,2,6,6-tetramethyl-4-acetamidopiperidinium) DTPA; 1-hydroxy-2,2,6,6-tetramethyl-4-acetamidopiperidinium EDTA; bis(1-hydroxy-2,2,6,6-tetramethyl-4-acetamidopiperidinium) EDTA; tris(1-hydroxy-2,2,6,6-tetramethyl-4-acetamidopiperidinium) EDTA; tetrakis(1-hydroxy-2,2,6,6-tetramethyl-4-hydroxypiperidinium) EDTA; 1-hydroxy-2,2,6,6-tetramethyl-4-acetoxypiperidinium citrate; bis(1-hydroxy-2,2,6,6-tetramethyl-4-acetoxypiperidinium)citrate; tris(1-hydroxy-2,2,6,6-tetramethyl-4-acetoxypiperidinium)citrate; 1-hydroxy-2,2,6,6-tetramethyl-4-acetoxypiperidinium DTPA; bis(1-hydroxy-2,2,6,6-tetramethyl-4-acetoxypiperidinium) DTPA; tris(1-hydroxy-2,2,6,6-tetramethyl-4-acetoxypiperidinium) DTPA; tetrakis(1-hydroxy-2,2,6,6-tetramethyl-4-acetoxypiperidinium) DTPA; pentakis(1-hydroxy-2,2,6,6-tetramethyl-4-acetoxypiperidinium) DTPA; 1-hydroxy-2,2,6,6-tetramethyl-4-acetoxypiperidinium EDTA; bis(1-hydroxy-2,2,6,6-tetramethyl-4-acetoxypiperidinium) EDTA; tris(1-hydroxy-2,2,6,6-tetramethyl-4-acetoxypiperidinium) EDTA and tetrakis(1-hydroxy-2,2,6,6-tetramethyl-4-acetoxypiperidinium) EDTA.

The above named counter-ions are ethylenediaminetetraacetic acid (EDTA), diethylenetriaminepentaacetic acid (DTPA), hydroxyethylethylenediaminetriacetic acid (HEDTA), nitrilotriacetic acid (NTA) or diethylenetriaminepentamethylenephosphonic acid (DTPMPA).

The organic UV absorber component ($c_1$) is preferably selected from butyl methoxydibenzoylmethane, ethylhexyl methoxydibenzoylmethane and isopropyl dibenzoylmethane Component ($c_1$) is most preferably selected from 4tert-butyl-4'-methoxydibenzoylmethane and 4-ethylhexyl-4'-methoxydibenzoylmethane. Most preferred is 1-(4-tert-butylphenyl)-3-(4-methoxyphenyl)propane-1,3-dione.

Component ($c_2$) is preferably selected from octyl methoxycinnamate (4-methoxycinnamic acid 2-ethylhexyl ester), diethanolamine methoxycinnamate (diethanolamine salt of 4-methoxycinnamic acid), isoamyl p-methoxycinnamate (4-ethoxycinnamic acid 2-isoamyl ester), 2,5-diisopropylmethyl cinnamate and a cinnamic acid amido derivative, and most preferably octyl methoxycinnamate.

Component ($c_3$) is preferably selected from 4-methyl-benzylidene camphor (3-4'-methyl)-benzylidene-bornan-2-one), 3-benzylidene camphor (3-benzylidene-bornan-2-one), polyacrylamidomethylbenzylidene camphor {N-[2(and 4)-2-oxyborn-3-ylidene-methyl)benyl]-acrylamide polymer}, trimonium-benzylidene camphor sulfate [3-(4'-trimethylammonium)-benzylidene-bornan-2-one methyl sulfate], terephthalydene dicamphorsulfonic acid {3,3'-(1,4-phenylenedimethine)-bis(7,7-dimethyl-2-oxo-bicyclo[2.2.1] heptane-1-methanesulfonic acid} or salts thereof, and benzylidene camphorsulfonic acid [3-(4'-sulfo)benzylidenebornan-2-one] or salts thereof, and most preferably from 4-methyl-benzylidene camphor.

Component ($c_4$) is preferably selected from diethylhexyl butamido Triazone and ethylhexyl triazone. Most preferably ethylhexyl triazone is used.

The organic UV filters according to component (c) can be used in admixture with other commercial available UV filters. Suitable UV absorbers which can be used are listed in the following Table:

TABLE 1

| Additional UV absorbers |
|---|
| p-aminobenzoic acid derivatives, for example 4-dimethylaminobenzoic acid 2-ethylhexyl ester |
| salicylic acid derivatives, for example salicylic acid 2-ethylhexyl ester |
| benzophenone derivatives, for example 2-hydroxy-4-methoxybenzophenone and its 5-sulfonic acid derivative |
| diphenylacrylates, for example 2-ethylhexyl 2-cyano-3,3- |

TABLE 1-continued

Additional UV absorbers diphenylacrylate, and 3-(benzofuranyl)2-cyanoacrylate
3-imidazol-4-yl acrylic acid and esters
benzofuran derivatives, especially 2-(p-amino-
phenyl)benzofuran derivatives, described in EP-A-582
189, US-A-5 338 539, US-A-5 518 713 and EP-A-613 893;
polymeric UV absorbers, for example the benzylidene
malonate derivatives described in EP-A-709 080
hydroxyphenyltriazine compounds, for example 2-(4'-
methoxyphenyl)-4,6-bis(2'-hydroxy-4'-n-octyloxyphenyl)-
1,3,5-triazine; 2,4-bis{[4-(3-(2-propyloxy)-2-
hydroxy-propyloxy)-2-hydroxy]-phenyl}-6-
(4-methoxyphenyl)-1,3,5-triazine; 2,4-bis{[4-
tris(trimethylsilyloxy-silylpropyloxy)-2-hydroxy]-phenyl}-6-
(4-methoxyphenyl)-1,3,5-triazine; 2,4-bis{[4-
(2''-methylpropenyloxy)-2-hydroxy]-phenyl}-6-(4-
methoxyphenyl)-1,3,5-triazine; 2,4-bis{[4-(1',1',1',3',5',5',5'-
heptamethyltrisilyl-2''-methyl-propyloxy)-2-
hydroxy]-phenyl}-6-(4-methoxyphenyl)-1,3,5-triazine
benzotriazole compounds, for example 2,2'-methylene-bis(6-
(2H-benzotriazol-2-yl)-4-(1,1,3,3-tetramethylbutyl)-phenol
2-phenylbenzimidazole-5-sulfonic acid and salts thereof
menthyl o-aminobenzoates Preferably mixtures of dibenzoylmethane derivatives (component $c_1$) with diphenylacrylates;

dibenzoylmethane derivatives (component $c_1$) with cinnamic acid esters (component $c_2$) are used.

The present compositions may comprise further traditional additives, for example antioxidants.

Accordingly, the present invention further pertains to a stabilized composition comprising (a) a body care product, household product, institutional & industrial products, textile or fabric,
(b) an effective stabilizing amount of at least one compound selected from the group consisting of
  (i) hindered nitroxyl compounds of formula (I),
  (ii) hindered hydroxylamine compounds of formula (II) and
  (iii) hindered hydroxylamine salt compounds of formula (III),
(c) an organic UV filter selected from
  ($c_1$) dibenzoylmethane derivatives;
  ($c_2$) cinnamic acid esters;
  ($c_3$) camphor derivatives; and
  ($c_4$) trianilino-s-triazine derivatives; and
(d) at least one compound selected from the group consisting of antioxidants, tocopherol, tocopherol acetate, hindered amine light stabilizers, complex formers, optical brighteners, surfactants, and polyorganosiloxanes.

Additional suitable antioxidants are for example selected from the hindered phenolic and benzofuranone stabilizers.

Suitable antioxidants are for example selected from the group consisting of

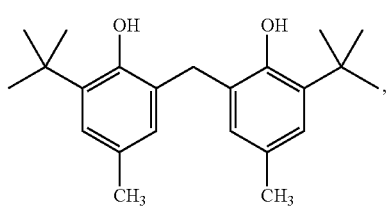

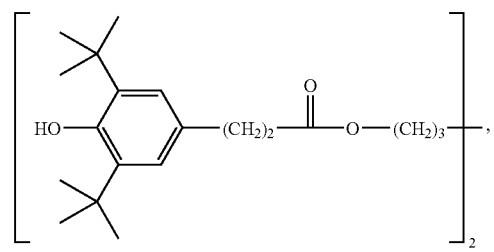

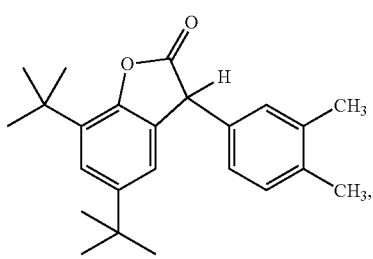

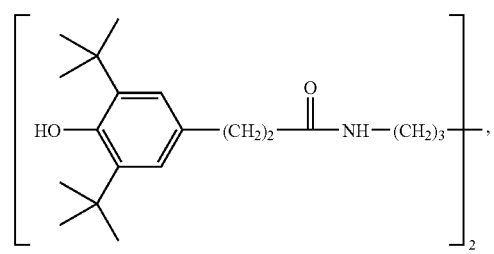

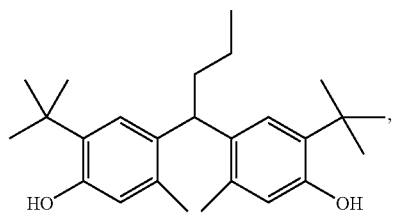

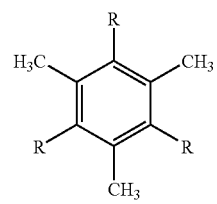

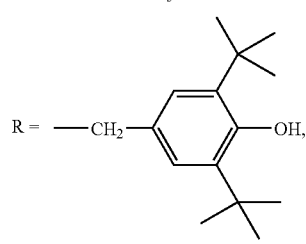

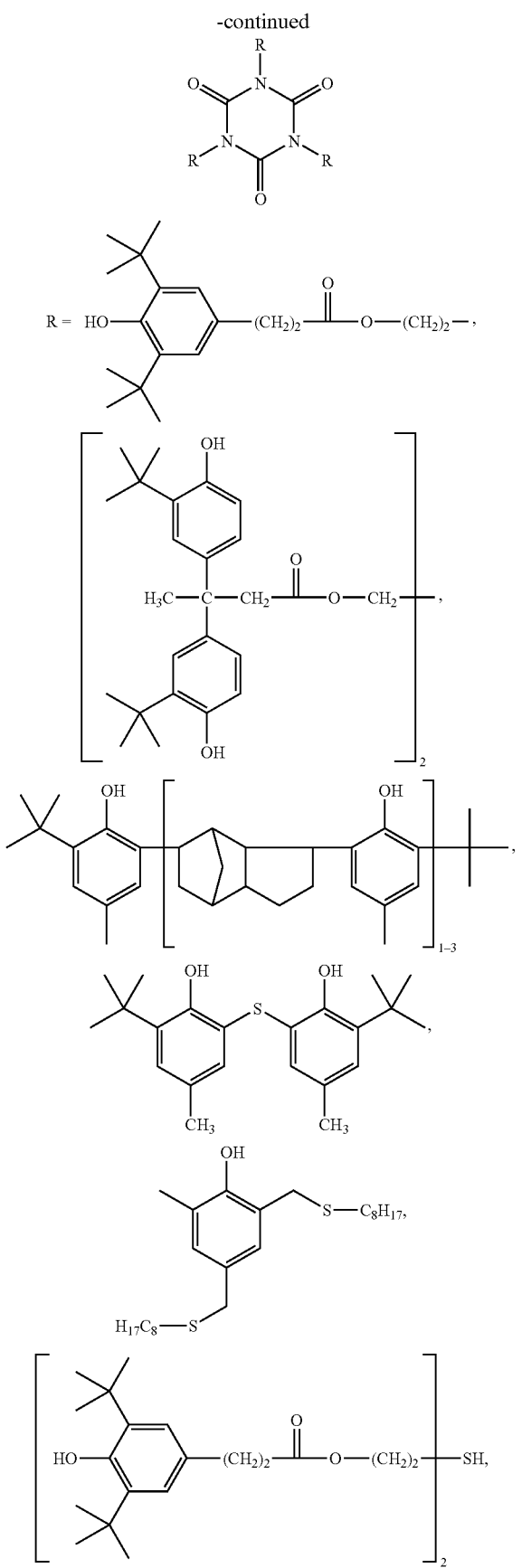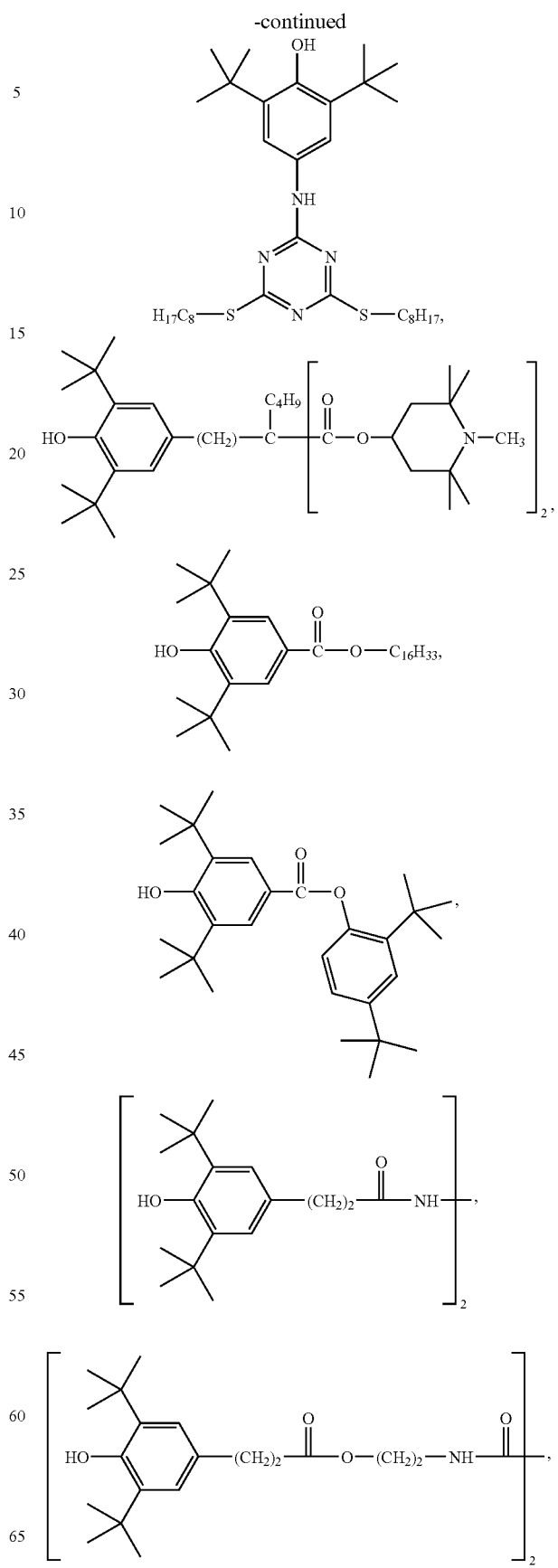

-continued

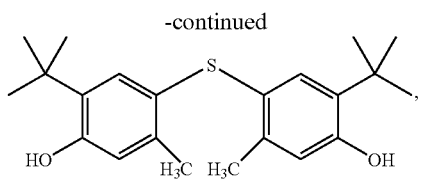

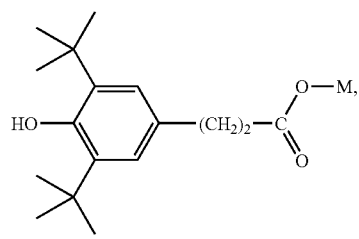

M = H, ammonium, alkali

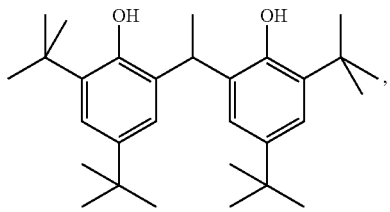

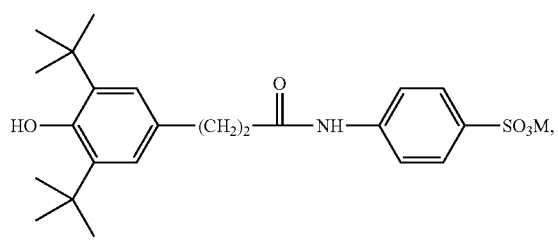

M = H, Na

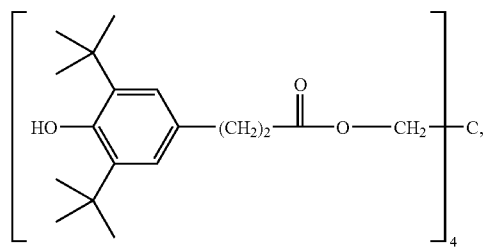

-continued

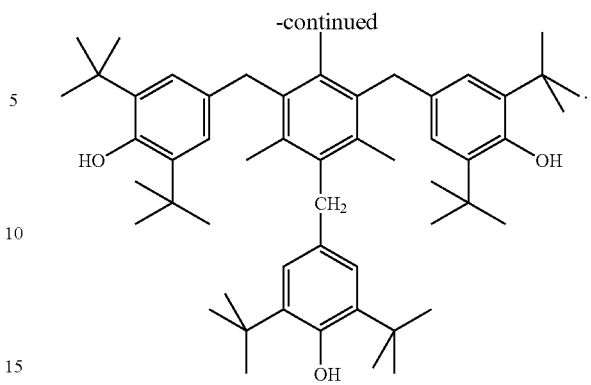

The hindered amine light stabilizers (HALS) of component (d) are for example known commercial compounds. They are for example selected from the group consisting of bis(2,2,6,6-tetramethylpiperidin-4-yl)sebacate, bis(2,2,6,6-tetramethylpiperidin-4-yl)succinate, bis(1,2,2,6,6-pentamethylpiperidin-4yl)sebacate, n-butyl-3,5-di-tert-butyl-4-hydroxybenzylmalonic acid-bis(1,2,2,6,6-pentamethylpiperidyl)ester, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino) ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]-decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4,5] decane, the reaction product of 7,7,9,9-tetramethyl-2-cycloundecyl-1-oxa-3,8-diaza-4-oxospiro[4,5]decane and epichlorohydrin, tetra(2,2,6,6-tetramethylpiperidin-4-yl)-butane-1,2,3,4-tetracarboxylate, tetra(1,2,2,6,6-pentamethylpiperidin-4-yl)-butane-1,2,3,4-tetracarboxylate, 2,2,4,4-tetramethyl-7-oxa-3,20-diaza-21-oxo-dispiro[5.1.11.2]-heneicosan, 8-acetyl-3-dodecyl-1,3,8-triaza-7,7,9,9-tetramethylspiro[4,5]decane-2,4-dione,

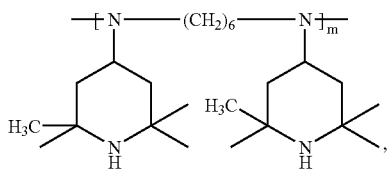

wherein m is a value from 5-50,

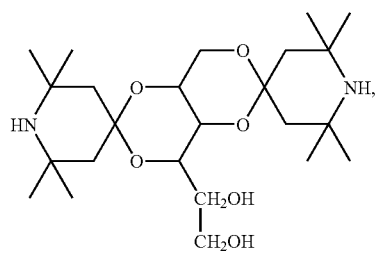

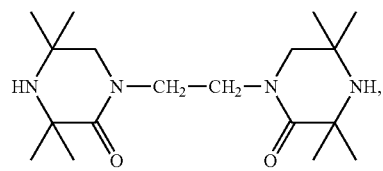

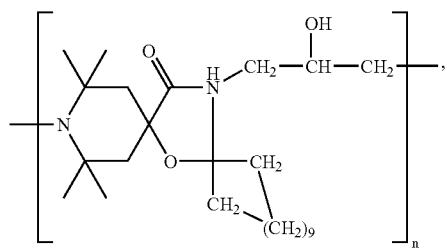

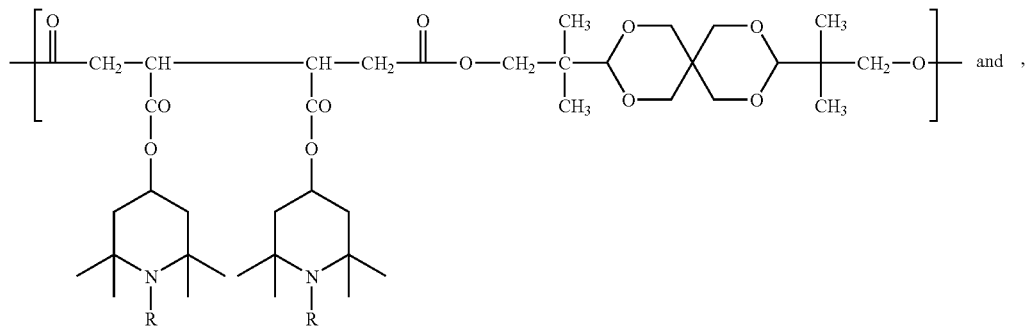

where R = H or CH₃

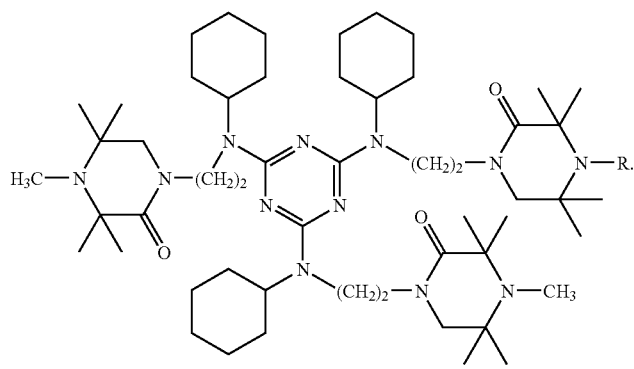

where R = H or CH₃

The complex formers of component (d) are for example nitrogen-containing complex formers or polyanionically-derived natural polysaccharides, for example those containing phosphate, phosphonate or methylphosphonate groups, such as chitin derivatives, e.g. sulfochitin, carboxymethylchitin, phosphochitin or chitosan derivatives, for example sulfochitosan, carboxymethylchitosan or phosphochitosan.

The complex formers are for example selected from the group consisting of ethylenediaminetetracetic acid (EDTA), nitrilotriacetic acid (NTA), -alaninediacetic acid (EDETA) or ethylenediaminedisuccinic acid (EDDS)

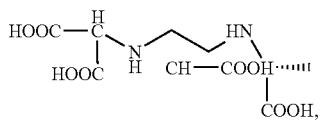

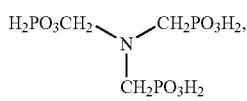

aminetrimethylenephosphoric acid (ATMP) conforming to formula

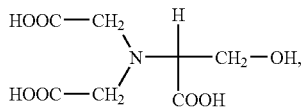

serinediacetic acid (SDA) conforming to formula

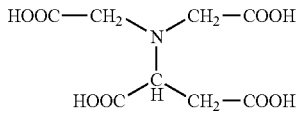

asparaginediacetic acid conforming to formula

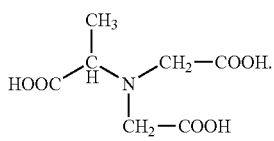

and methylglycinediacetic acid (MGDA) conforming to formula

The present stabilizer systems are particularly suitable for stabilizing body care products, in particular for use in skin-care products, as bath and shower products, preparations containing fragrances and odoriferous substances, hair-care products, dentifrices, deodorizing and antiperspirant preparations, decorative preparations, light protection formulations and preparations containing active ingredients.

Suitable skin-care products are, in particular, body oils, body lotions, body gels, treatment creams, skin protection ointments, shaving preparations, such as shaving foams or gels, skin powders, such as baby powder, moisturising gels, moisturising sprays, revitalising body sprays, cellulite gels and peeling preparations.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, like tocopherol, ascorbic acid, vitamin Q, D and K, carotinoid such as retinol, retinal, retinoic acid and licopen, vegetable extract preparations, antibacterial preparations, preparations containing instable aminoacids comprising dipeptides, oligopepeptides and polypeptides such as methionen, cyctein, cystin, tryptophan, phenylalanin, tyrosin, preparations containing phenols, poylphenols or flavonoids.

A further aspect of the present invention is the stabilization of active ingredients selected from vitamins, carotinoids, vegetable extracts, antibacterials, phenols, poylphenols or flavonoids comprising applying thereto at least one compound of component (b) and at least one compound of component (c).

The present body care products can be in the form of creams, ointments, pastes, foams, gels, lotions, powders, make-ups, sprays, sticks or aerosols or wipes. The present stabilizer systems may be present in the oil phase or in the aqueous or aqueous/alcoholic phase.

The additives of component (b) and (c) are present, for example, in the body care and household products in a concentration of about 5 to about 10000 ppm, based on the total formulation, preferably from about 10 to about 5000 ppm, and most preferably from about 100 to about 1000 ppm.

For example the additives of component (b) and (c) are present in the body care and household products in a concentration of about 5, 10, 15, 20, 25, 35, 40, 45 or 50 ppm, based on the total formulation.

For example, the additives of component (b) and (c) is present from about 5 to about 1000 ppm in the formulations (compositions) of this invention.

The ratio of component (b) to component (c) is in the present composition is from 1:1000 to 1000:1, preferably from 1:100 to 100:1, most preferably from 1:10 to 10:1, Additionally, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palinitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butyistearate, n-hexyllaurate, n-decyloleate, isooctylstearate, iso-nonyistearate, isononyl isononanoate, 2-ethylhexylpalmitate, 2-hexyllaurate, 2-hexyldecylstearate, 2-octyidodecylpalmitate, oleyloleate, oleylerucate, erucyloleate, erucylerucate, cateary1 octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants diethylhexyl 2,6-naphthalate, di-n-butyl adipate, di(2-ethylhexyl)adipate, di(2-ethylhexyl)-succinate and diisotridecyl acelaat, and also diol esters, such as ethylene glycol dioleate, ethylene glycol dilsotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated ancvor unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups, or iminodisuccinic acid and imiondisuccinic acid salts [CAS 7408-20-0] or latex partides.

Natural or Synthetic Triglycerides Including Glyceryl Esters and Derivatives

Di- or tri-glycerides, based on $C_6$-$C_{18}$ fatty acids, modified by reaction with other alcohols (caprylictcapric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Akylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), pefrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Coming 200 fluid, Rhodia Mirasil DM), dimethiconol, cyclic silicone fluids, cyclopentasiloxanes volatiles (Dow Coming 345 fluid), phenyltrimethicone (Dow Coming 556 fluid). Also suitable are simethicones, which are mixtures of dimethicones having an average chain length of from 200 to 300 dimnethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifer systems may comprise for example: carbocyclic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, dilsostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohoilcetearyl glucoside. W/O emulsifiers such as methyl glucose dioleate/methyl glucose isostearate. Sulfates and sulfonated derivatives, dialkylsulfosuccinates, dioclyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quatemary ammonium such as cetyltrimethylbroide amonium broide (CTBA), stearylalkonium. Amide derivatives, alkanolamides such as acylamide DEA, ethoxylated amides such as PEG-n acylamide, oxydeamide. Polysiloxanelpolyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylamino-propyl-N,N-dimethylammonium glycinates, cocoacylaminopropyldimethylammonium glycinate and 2-alkyl-3-carboxymethyl-3-hydroxyethylimidazolines each having from 8 to 18 arbon atoms in the alkyl or acyl group and also cocoacylaminoethylhydroxyethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251.

Nonionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and steareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanefte N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic/pharmaceutical preparations, for example creams, gels, lotions, alcoholic and aqueous/alcoholic solutions, emulsions, wax/fat compositions. stick preparations, powders or ointments, may in addition contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, antimicrobial agents and the like.

Super-fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, monoand/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropylmethylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80(stearech-10 allyl ether/acrylates copolymer), Salcare SC81(acrylates copolymer), Salcare SC91 and Salcare AST(sodium acrylates copolymer/PPG-1 trideceth-6), sepigel 305(polyacrylamide/laureth-7), Simulgel NS and Simulgel EG (hydroxyethyl acrylate/sodium acryloyidimethyl taurate copolymer), Stabilen 30 (acrylates/vinyl isodecanoate crosspolymer), Pemulen TR-1(acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quartemised vinyl-pyrrolidone/vinyl imidazole polymers, for example Luviquat® (BASF), condensation products of polyglycols and amines, quatemised collagen polypeptides, for example lauryidimonium hydroxypropyl hydrolyzed collagen (Lamequat®L/Grünau), quatemised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyidiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert-butylaminoethyl methacrylate/2-hydroxypropyl methacrylate copolymers, polyvinylpyrrolidone, vinylpyrrolidone/-vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biocienic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available comercially, for example, an aluminium chlorohydrate corresponding to formula $Al_2(OH)_5Cl \times 2.5\ H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic adid, tartaric acid or tartaric acid diethyl ester. Antibacterial active ingredients that influence the germ flora and kill or inhibit the growth of sweat-decomposing bacteria can likewise be present in the preparations (especially in stick preparations). Examples indude chitosan, phenoxyethanol and chlorhexidine gluconate. 5-chloro-2-(2,4-dichlorophenoxy)-phenol (Triclosan, Irgasan, Ciba Specialty Chemicals Inc.) has also proved especially effective.

Anti-dandruff Agents

As anti-dandruff agents there may be used, for example, dimbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quatemary cellulose derivatives containing a high proportion of acrylic acid, collagen, hyaluronic acid and salts thereof and similar compounds.

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that corne into consideration for that purpose have preferably from 2 to 15 carbon atoms and at least two hydroxy groups. The polyols ay also contain further functional groups, especially arnino groups, and/or may be modified with nitrogen. Typical examples are as follows:

glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for exam ple sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives

Suitable preservatives include, for example, Methyl-, Ethyl-, Propyl-, Butyl- parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyidibromoglutanitrile, Phenoxyethanol, Sodium Hydroxymethylglycinate, Irmidazolidinyl Urea, Tridosan and further substance classes listed in the following reference: K. F. DePolo—A short textbook of cosmetology, Chapter 7, Table 7-2, 7-3, 7-4 and 7-5, p 210-219.

Bacteria-inhibiting Agents

Typical examples of bacteria-inhibiting agents are preservatives that have a specific action against gram-positive bacteria, such as 2,4,4'-trichloro-2'-hydroxydiphenyl ether, chlorhexidine(1,6-di(4-chlomphenyl-biguanido)hexane) or TCC (3,4,4'-trichlorocarbanilide). A large number of aromatic substances and ethereal oils also have antimicrobial properties. Typical examples are the active ingredients eugenol, menthol and thymol in dove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons indude mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cydovertal, lavandin oil, muscatel sage oil, damascone, bourbon geranium oil, cydohexyl salicylate, vertofix coeur, iso-E-Super, Fixolide NP, evemyl, iraldein gamma, phenylacetic acid, geranyl acetate, benzyl acetate, rose oxide, romillat, irotyl and floramat alone or in admixture with one another.

Other Adjuvants

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, propellants, such as propane/butane mixtures, $N_2O$, dimethyl ether, $CO_2$, $N_2$ or air, so-wlled coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetonetprecursors as described in WO 01/85124 and/or erythrulose.

The present stabilizer systems are particularly suitable for stabilizing body care products, in particular:
  skin-care preparations, e.g. skin-washing and deansing preparations in the form of tablet-form or liquid soaps, soapless detergents or washing pastes,
  bath preparations, e.g. liquid (foam baths, milks, shower preparations) or solid bath preparations, e.g. bath cubes and bath salts;
  skin-care preparations, e.g. skin emulsions, multi-emulsions or skin oils; body oils, body lotions, body gels; skin protection ointments;
  cosmetic personal care preparations, e.g. facial make-up in the form of day creams or powder creams, face powder (loose or pressed), rouge or cream rnake-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances and odoriferous substances containing preparations (scents, eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, halrsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile;

dentifrices, in particular tooth creams, toothpastes, mouth-washes, mnouth rinses, anti-plaque preparations and cleaning agents for dentures;

decorative preparations, in particular lipsticks, nail varnishes, eye shadows, mascaras, dry and moist make-up, rouge, powders, depilatory agents and suntan lotions cosmetic formulations containing active ingredients, in particular hormone preparations, vitamin preparations, vegetable extract preparations and antibacterial preparations.

Suitable cosmetic formulations containing active ingredients are in particular hormone preparations, vitamin preparations, vegetable extract preparations and antibacterial preparations.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a stick, in the form of a spray (spray with propellent gas or pump-action spray) or an aerosol, in the form of a foam, or in the form of a paste.

Of special importance as cosmetic preparations for the skin are lightprotective preparations, such as sun milks, lotions, creams, wipes, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the fbrm of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of component (b) according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of component (b) according to the invention, optionally a UV absorber according to Tables 1-3, PEG-6-$C_{10}$oxoalcohol and sorbitan sesquioleate, to which water and any desired quaternary ammonium compound, for example 4% minkamidopropyl dimethyl-2-hydroxyethylammonium chloride or Quatemium 80 is added;

$a_2$) spontaneously emulsifying stock formulation consisting of component (b) according to the invention, optionally a UV absorber according to Tables 1-3, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

b) quat-doped solutions of component (b) according to the invention in butyl triglycol and tributyl citrate; and optionally a UV absorber according to Tables 1-3;

c) mixtures or solutions of component (b) according to the invention with n-alkylpyrrolidone;

and optionally a UV absorber according to Tables 1-3.

Laundry detergents, laundry adjuncts, laundry pre-treatment products, laundry boosters, fabric treatments (eg., spray starches, fabric refreshers), fabric softeners or other products, from which the additives of component (b) and (c) are intended for deposition onto fabrics with use, are considered household products of this invention, and the above concentration levels also pertain thereto. The present additives of component (b) and (c) are effective at stabilizing the laundry detergents and fabric softeners, as well as the fabrics treated therewith.

The following is a list of examples of body care products of this invention and their ingredients:

| Body care product | Ingredients |
|---|---|
| moisturising cream | vegetable oil, emulsifier, thickener, perfume, water, antioxidant, UV absorbers |
| shampoo | surfactant, emulsifier, preservatives, perfume, antioxidant, uv absorbers |
| toothpaste | cleaning agent, thickener, sweetener, flavour, colorant, antioxidant, water, UV absorbers |
| lip-care stick | vegetable oil, wax, $TiO_2$, antioxidant, UV absorbers |

The present body care products, household products, textiles and fabrics have high stability towards color changes and chemical degradation of the ingredients present in these products. For example, present compositions that comprise a dye are found to have excellent color stability.

Accordingly, the present invention further pertains to a stabilized composition comprising
(a) a body care product, household product, textile or fabric,
(b) an effective stabilizing amount of at least one compound selected from the group consisting of
   (i) hindered nitroxyl compounds of formula (I),
   (ii) hindered hydroxylamine compounds of formula (II) and (iii) hindered hydroxylamine salt compounds of formula (III),
(c) an organic UV filter selected from
   ($c_1$) dibenzoylmethane derivatives;
   ($c_2$) cinnamic acid esters;
   ($c_3$) camphor derivatives;
   ($c_4$) trianilino-s-triazine derivatives; and
(e) a dye.

Dyes according to the present invention are for example:
inorganic pigments, for example iron oxide (Iron Oxide Red, Iron Oxide Yellow, Iron Oxide Black, etc.), Ultramarines, Chromium Oxide Green or Carbon Black;
natural or synthetic organic pigments;
disperse dyes which may be solubilzed in solvents like direct hair dyes of the HC type, for example HC Red No. 3, HC Blue No. 2 and all other hair dyes listed in International Cosmetic Ingredient Dictionary and Handbook, $7^{th}$ edition 19997) or the dispersion dyes listed in Color Index International or Society of Dyers and Colourists;
color varnishes (insoluble salts of soluble dyes, like many Ca-, Ba- or Al-salts of anionic dyes);
soluble anionic or cationic dyes, like acid dyes (anionic), basic dyes (cationic), direct dyes, reactive dyes or solvent dyes;
fluorescent dyes;
fluorescein; and
isothiocyanates.

Generally, for the coloration of household- and body care products all substances are suitable which have an absorption in the visible light of electromagnetic radiation (wavelength of ca. 4000 to 700 nm). The absorption is often caused by the following chromophores: Azo-(mono-, di, tris-, or poly-)stilbene-, carotenoide-, diarylmethan-, triarylmethan-, xanthen-, acridin-, quinoline, methin-(also polymethin-), thiazol-, indamin-, indophenol-, azin-, oxazin, thiazin-, anthraquinone-, indigoid-, phtalocyanine- and further synthetic, natural and/or inorganic chromophores.

The present stabilizer systems are also used in household cleaning and treatment agents, for example in laundry products and fabric softeners, liquid cleansing and scouring agents, glass detergents, neutral cleaners (all-purpose cleaners), acid household cleaners (bath), bathroom cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-are products, rug cleaners and carpet shampoos, agents for removing rust, color and stains (stain remover salt), furniture and multipurpose polishes and leather and vinyl dressing agents (leather and vinyl sprays) and air fresheners.

The present invention also concerns home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets. The present invention also relates to home care products such as candles, gel candles, air fresheners and fragrance oils (for the home).

The stabilizers of the present invention may be employed in fabric treatment that takes place after use of the fabric, referred to as fabric care. Such treatments include laundering, which uses detergents, laundry aids and/or fabric conditioner, and the application of non-detergent based fabric care products, such as spray-on products. When employed in this fashion, the present stabilizers are intended for deposition onto the fabric and used to protect the fabric, colorants and fragrances associated with said these fabrics from environmental damage.

Typical examples of household cleaning and treating agents are:

| Household cleaners/ household treating agents | Ingredients |
|---|---|
| detergent concentrate | surfactant mixture, ethanol, antioxidant, water, UV absorbers, antioxidant |
| shoe polish | wax, wax emulsifier, antioxidant, water, preservative, UV absorbers, antioxidant |
| wax-containing floor | emulsifier, wax, sodium chloride, antioxidant, water, |
| cleaning agent | preservative, UV absorbers, antioxidant |

The present stabilizers are for example incorporated by dissolution in an oil phase or alcoholic or water phase, where required at elevated temperature.

The present invention also pertains to a method of stabilizing a body care product, household product, textile or fabric, which comprises incorporating therein or applying thereto at least one compound of component (b) and at least one compound of component (c), preferably at least one compound of the formulae A to EE and A* to EE*.

Preferably a dibenzoylmethane derivative (=component $c_1$), most preferably 1-(4-tert-butylphenyl)-3-(4-methoxyphenyl)propane-1,3-dione is used as component (c).

In the case of stabilized fabrics, for example dyed fabrics, the present stabilizers are applied thereto via deposition from for instance detergents, fabric conditioners or non-detergent based fabric care products.

The present fabrics are natural or synthetic, and may be woven or nonwoven.

The present invention also pertains to a method of stabilizing a body care product, household product, textile or fabric, each of which contain a dye, which comprises incorporating therein or applying thereto at least one compound of the formulae (I), (II) and (Ill) (=component (b)), and at least one compound of component (c), for example at least one compound of the formulae A to EE and A* to EE* and at least one compound of component (c).

Preferably a dibenzoylmethane derivative (=component $c_1$) is used as component (c) and most preferably 1-(4-tert-butylphenyl)-3-(4-methoxyphenyl)propane-1,3-dione.

The stabilizers of formulae (I), (II) and (III) (=component (b)) together with the organic UV absorbers (component (c)) are very effective towards the stabilization of dyes in the present compositions.

The textiles of this invention are for example textile fiber materials, for example nitrogen containing or hydroxy-group-containing fiber materials, for instance textile fiber materials selected from cellulose, silk, wool, synthetic polyamides, leather and polyurethanes. Included are cotton, linen and hemp, pulp and regenerated cellulose. Included also are cellulosic blends, for example mixtures of cotton and polyamide or cotton/polyester blends.

The additives of the present invention are for example applied to textiles in a dyeing or printing process, or in a finishing process. For instance, the additives may be applied as part of a dye formulation. The additives may be applied to textiles for example in an ink-jet printing process. The additives are for example applied as part of an aqueous dye solution or printing paste. They may be applied in an exhaust method or dyeing by the padder dyeing method, in which the textiles are impregnated with aqueous dye solutions, which may contain salts, and the dyes and additives are fixed, after an alkali treatment or in the presence of alkali, if appropriate with the action of heat or by storage at room temperature for several hours. After fixing, the dyeings or prints are rinsed thoroughly with cold and hot water, if appropriate with the addition of an agent which has a dispersing action and promotes diffusion of the non-fixed portions.

The dye or ink formulations for application to textiles may comprise further customary additves, for example surfactants, antifoams, antimicrobials and the like, for example as disclosed in U.S. Pat. Nos. 6,281,339, 6,353,094 and 6,323,327, the disclosures of which are hereby incorporated by reference.

A further aspect of the present invention is the photo stabilizing of the UV filters according to component (c).

Therefore, the present invention also pertains to a method of photo stabilizing a compound according to component (c), which comprises applying to this compound at least one compound of component (b).

The following Examples illustrate the invention. Percentages are in weight percent unless indicated otherwise.

EXAMPLES

The following stabilizers are employed in the Examples below:

A. Amine Compound (=Component (b)):

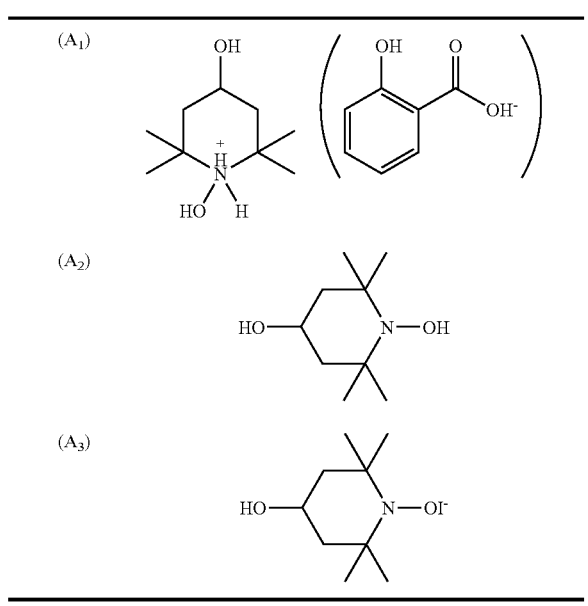

B. Organic UV Absorber (=Component (c)):

| | |
|---|---|
| ($B_1$) | Ethylhexyl Methoxy Cinnamate |
| ($B_2$) | Butyl Methoxydibenzoylmehtane |
| ($B_3$) | 4-Methylbenzyliden Camphor |
| ($B_4$) | Ethylhexyl Triazone |
| ($B_5$) | Mixture of Ethylhexyl Methoxy Cinnamate and Butyl Methoxydibenzoylmehtane |
| ($B_6$) | Mixture of Butyl Methoxydibenzoylmehtane and Octocrylene |

EXAMPLES 1–6

Preparation of a toilet water

| | Examples | | | | | |
|---|---|---|---|---|---|---|
| Ingredients (w/w) % | 1 | 2 | 3 | 4 | 5 | 6 |
| ethanol, 96% | 60 | 60 | 60 | 60 | 60 | 60 |
| d-limonene | 5 | 5 | 5 | 5 | 5 | 5 |
| cedrene | 1.5 | 1.5 | 1.5 | 1.5 | 1.5 | 1.5 |
| citronellol | 0.5 | 0.5 | 0.5 | 0.5 | 0.5 | 0.5 |
| savin | 0.5 | 0.5 | 0.5 | 0.5 | 0.5 | 0.5 |
| stabilizer ($A_1$), ($A_2$) or ($A_3$) | 0.08 | 0.08 | 0.08 | 0.08 | 0.08 | 0.08 |
| Organic UV filter ($B_1$) | 0.1 | | | | | |
| Organic UV filter ($B_2$) | | 0.1 | | | | |
| Organic UV filter ($B_3$) | | | 0.1 | | | |

EXAMPLES 1–6-continued

Preparation of a toilet water

| Ingredients (w/w) % | \multicolumn{6}{c}{Examples} |
|---|---|---|---|---|---|---|
| | 1 | 2 | 3 | 4 | 5 | 6 |
| Organic UV filter ($B_4$) | | | | 0.1 | | |
| Organic UV filter ($B_5$) | | | | | 0.1 | |
| Organic UV filter ($B_6$) | | | | | | 0.1 |
| S,S-EDDS | 0.005 | 0.005 | 0.005 | 0.005 | 0.005 | 0.005 |
| colorant (D&C Yellow No. 5) | 0.02 | 0.02 | 0.02 | 0.02 | 0.02 | 0.02 |
| water | ad. 100 | ad. 100 | ad. 100 | ad. 100 | ad.100 | ad. 100 |

The components are thoroughly mixed in the cited sequence at 50° C., a clear homogeneous solution being obtained. Excellent results are achieved.

EXAMPLES 7-12

Preparation of a hair styling spray

| Ingredients (w/w) % | 7 | 8 | 9 | 10 | 11 | 12 |
|---|---|---|---|---|---|---|
| alcohol, anhydrous | 96.21 | 96.21 | 96.21 | 96.21 | 96.21 | 96.21 |
| octylacrylamide/acrylate/butylamino ethylmethacrylate copolymer | 2.52 | 2.52 | 2.52 | 2.52 | 2.52 | 2.52 |
| hydroxypropyl cellulose | 0.51 | 0.51 | 0.51 | 0.51 | 0.51 | 0.51 |
| aminomethylpropanol (95%) | 0.46 | 0.46 | 0.46 | 0.46 | 0.46 | 0.46 |
| stabilizer ($A_1$), ($A_2$) or ($A_3$) | 0.05 | 0.05 | 0.05 | 0.05 | 0.05 | 0.05 |
| Organic UV filter ($B_1$) | 0.05 | | | | | |
| Organic UV filter ($B_2$) | | 0.05 | | | | |
| Organic UV filter ($B_3$) | | | 0.05 | | | |
| Organic UV filter ($B_4$) | | | | 0.05 | | |
| Organic UV filter ($B_5$) | | | | | 0.05 | |
| Organic UV filter ($B_6$) | | | | | | 0.05 |
| perfume oil | 0.20 | 0.20 | 0.20 | 0.20 | 0.20 | 0.20 |

The hydroxypropyl cellulose is first predissolved in half of the alcohol Vortex mixer) and is charged with the aminomethylpropanol. The other components—with the exception of the acrylate resin—are dissolved in alcohol and this solution is added, with stirring, to the hydroxypropyl cellulose. Subsequently, the acrylate resin is added and stirred until completely dissolved. Excellent results are achieved.

EXAMPLES 13-18

Preparation of a shampoo for greasy hair

| Ingredients (w/w) % | 13 | 14 | 15 | 16 | 17 | 18 |
|---|---|---|---|---|---|---|
| sodium myreth sulfate | 50.00 | 50.00 | 50.00 | 50.00 | 50.00 | 50.00 |
| TEA abietoyl collagen hydrolysate | 3.50 | 3.50 | 3.50 | 3.50 | 3.50 | 3.50 |
| laureth-3 | 3.00 | 3.00 | 3.00 | 3.00 | 3.00 | 3.00 |
| colorant (D&C Red No. 33) | 0.20 | 0.20 | 0.20 | 0.20 | 0.20 | 0.20 |
| stabilizer ($A_1$), ($A_2$) or ($A_3$) | 0.05 | 0.05 | 0.05 | 0.05 | 0.05 | 0.05 |
| Organic UV filter ($B_1$) | 0.15 | | | | | |
| Organic UV filter ($B_2$) | | 0.15 | | | | |
| Organic UV filter ($B_3$) | | | 0.15 | | | |
| Organic UV filter ($B_4$) | | | | 0.15 | | |
| Organic UV filter ($B_5$) | | | | | 0.15 | |
| Organic UV filter ($B_6$) | | | | | | 0.15 |
| phosphonomethylchitosan, sodium salt | 0.01 | 0.01 | 0.01 | 0.01 | 0.01 | 0.01 |
| perfume oil | 0.10 | 0.10 | 0.10 | 0.10 | 0.10 | 0.10 |
| water | ad. 100 | ad. 100 | ad. 100 | ad. 100 | ad. 100 | ad. 100 |

The components are mixed, with stirring, at room temperature until they are completely dissolved. The pH is 6.5. Excellent results are achieved.

EXAMPLES 19-24

Preparation of a baby shampoo

| Ingredients (w/w) % | Examples |  |  |  |  |  |
|---|---|---|---|---|---|---|
|  | 13 | 14 | 15 | 16 | 17 | 18 |
| cocoamidopropylbetaine | 35.00 | 35.00 | 35.00 | 35.00 | 35.00 | 35.00 |
| water, deion. | ad. 100 | ad. 100 | ad. 100 | ad. 100 | ad. 100 | ad. 100 |
| citric acid | q.s. (pH) | q.s. (pH) | q.s. (pH) | q.s. (pH) | q.s. (pH) | q.s. (pH) |
| polyquaternium-15 | 0.15 | 0.15 | 0.15 | 0.15 | 0.15 | 0.15 |
| perfume oil | 0.30 | 0.30 | 0.30 | 0.30 | 0.30 | 0.30 |
| chlorophyll | 0.20 | 0.20 | 0.20 | 0.20 | 0.20 | 0.20 |
| stabilizer $(A_1)$, $(A_2)$ or $(A_3)$ | 0.05 | 0.05 | 0.05 | 0.05 | 0.05 | 0.05 |
| Organic UV filter $(B_1)$ | 0.15 |  |  |  |  |  |
| Organic UV filter $(B_2)$ |  | 0.15 |  |  |  |  |
| Organic UV filter $(B_3)$ |  |  | 0.15 |  |  |  |
| Organic UV filter $(B_4)$ |  |  |  | 0.15 |  |  |
| Organic UV filter $(B_5)$ |  |  |  |  | 0.15 |  |
| Organic UV filter $(B_6)$ |  |  |  |  |  | 0.15 |
| antioxidant of formula (102) | 0.05 | 0.05 | 0.05 | 0.05 | 0.05 | 0.05 |
| colorant (D&C Yellow No. 5) | 0.02 | 0.02 | 0.02 | 0.02 | 0.02 | 0.02 |
| sodium chloride | 0.30 | 0.30 | 0.30 | 0.30 | 0.30 | 0.30 |

The components are mixed, with stirring, at room temperature until they are completely dissolved. The pH is 6.5. Excellent results are achieved.

EXAMPLES 25-30

Preparation of a green-colored glass detergent

| Ingredients (w/w) % | Examples |  |  |  |  |  |
|---|---|---|---|---|---|---|
|  | 25 | 26 | 27 | 28 | 29 | 30 |
| anionic/amphoteric surfactants (Lumorol RK) | 0.7 | 0.7 | 0.7 | 0.7 | 0.7 | 0.7 |
| butyl glycol | 5.0 | 5.0 | 5.0 | 5.0 | 5.0 | 5.0 |
| isopropanol | 20.0 | 20.0 | 20.0 | 20.0 | 20.0 | 20.0 |
| d-limonene | 4.00 | 4.00 | 4.00 | 4.00 | 4.00 | 4.00 |
| colorant (D&C Green No. 2) | 0.05 | 0.05 | 0.05 | 0.05 | 0.05 | 0.05 |
| stabilizer $(A_1)$, $(A_2)$ or $(A_3)$ | 0.05 | 0.05 | 0.05 | 0.05 | 0.05 | 0.05 |
| Organic UV filter $(B_1)$ | 0.05 |  |  |  |  |  |
| Organic UV filter $(B_2)$ |  | 0.05 |  |  |  |  |
| Organic UV filter $(B_3)$ |  |  | 0.05 |  |  |  |
| Organic UV filter $(B_4)$ |  |  |  | 0.05 |  |  |
| Organic UV filter $(B_5)$ |  |  |  |  | 0.05 |  |
| Organic UV filter $(B_6)$ |  |  |  |  |  | 0.05 |
| water, demin. | ad. 100 | ad. 100 | ad. 100 | ad. 100 | ad. 100 | ad. 100 |

Preparation: The components are dissolved in the indicated sequence until a clear homogeneous mixture is obtained.

EXAMPLES 31-36

Preparation of a floor wax

| Ingredients (w/w) % | Examples |  |  |  |  |  |
|---|---|---|---|---|---|---|
|  | 31 | 32 | 33 | 34 | 35 | 36 |
| wax mixture | 12 | 12 | 12 | 12 | 12 | 12 |
| white spirit | ad. 100 | ad. 100 | ad. 100 | ad. 100 | ad. 100 | ad. 100 |
| d-limonene | 4.00 | 4.00 | 4.00 | 4.00 | 4.00 | 4.00 |
| stabilizer $(A_1)$, $(A_2)$ or $(A_3)$ | 0.2 | 0.2 | 0.2 | 0.2 | 0.2 | 0.2 |
| Organic UV filter $(B_1)$ | 0.2 |  |  |  |  |  |

EXAMPLES 31-36-continued

Preparation of a floor wax

| Ingredients (w/w) % | 31 | 32 | 33 | 34 | 35 | 36 |
|---|---|---|---|---|---|---|
| Organic UV filter (B$_2$) |  | 0.2 |  |  |  |  |
| Organic UV filter (B$_3$) |  |  | 0.2 |  |  |  |
| Organic UV filter (B$_4$) |  |  |  | 0.2 |  |  |
| Organic UV filter (B$_5$) |  |  |  |  | 0.2 |  |
| Organic UV filter (B$_6$) |  |  |  |  |  | 0.2 |

Preparation: The components are stirred in the indicated sequence until a homogeneous mixture is obtained.

EXAMPLES 37-42

Preparation of an Eyeliner

| Ingredients (w/w) % | 37 | 38 | 39 | 40 | 41 | 42 |
|---|---|---|---|---|---|---|
| Polysaccharide resin (Kama KM 13, Kama) | 8.00 | 8.00 | 8.00 | 8.00 | 8.00 | 8.00 |
| Iron Oxide Black | 6.50 | 6.50 | 6.50 | 6.50 | 6.50 | 6.50 |
| Carnauba wax | 1.00 | 1.00 | 1.00 | 1.00 | 1.00 | 1.00 |
| Triethanolamin, 99% | 1.00 | 1.00 | 1.00 | 1.00 | 1.00 | 1.00 |
| Hydrogenated polyisobutane | 1.00 | 1.00 | 1.00 | 1.00 | 1.00 | 1.00 |
| Hydrogenated polydecene | 1.00 | 1.00 | 1.00 | 1.00 | 1.00 | 1.00 |
| Sorbitan sesquioleate | 1.00 | 1.00 | 1.00 | 1.00 | 1.00 | 1.00 |
| Xanthum gum | 0.50 | 0.50 | 0.50 | 0.50 | 0.50 | 0.50 |
| Carboxymethyl cellulose | 0.40 | 0.40 | 0.40 | 0.40 | 0.40 | 0.40 |
| Magnesium aluminium silicate | 0.40 | 0.40 | 0.40 | 0.40 | 0.40 | 0.40 |
| Methyl paraben | 0.35 | 0.35 | 0.35 | 0.35 | 0.35 | 0.35 |
| Stearic acid | 2.50 | 2.50 | 2.50 | 2.50 | 2.50 | 2.50 |
| Lecithin | 0.20 | 0.20 | 0.20 | 0.20 | 0.20 | 0.20 |
| Imidazolidinyl urea | 0.10 | 0.10 | 0.10 | 0.10 | 0.10 | 0.10 |
| stabilizer (A$_1$), (A$_2$) or (A$_3$) | 0.05 | 0.05 | 0.05 | 0.05 | 0.05 | 0.05 |
| Organic UV filter (B$_1$) | 0.1 |  |  |  |  |  |
| Organic UV filter (B$_2$) |  | 0.1 |  |  |  |  |
| Organic UV filter (B$_3$) |  |  | 0.1 |  |  |  |
| Organic UV filter (B$_4$) |  |  |  | 0.1 |  |  |
| Organic UV filter (B$_5$) |  |  |  |  | 0.1 |  |
| Organic UV filter (B$_6$) |  |  |  |  |  | 0.1 |
| Antioxidant of formula (100) | 0.05 | 0.05 | 0.05 | 0.05 | 0.05 | 0.05 |
| Water | ad. 100 | ad. 100 | ad. 100 | ad. 100 | ad. 100 | ad. 100 |

EXAMPLES 43-48

Preparation of a Nail Varnish

| Ingredients (w/w) % | 43 | 44 | 45 | 46 | 47 | 48 |
|---|---|---|---|---|---|---|
| Poly(1-trimethyl-silylpropylene) | 0.30 | 0.30 | 0.30 | 0.30 | 0.30 | 0.30 |
| Nitrocellulose | 12.00 | 12.00 | 12.00 | 12.00 | 12.00 | 12.00 |
| Alkyd resin | 10.00 | 10.00 | 10.00 | 10.00 | 10.00 | 10.00 |
| Dibutyl phthalate | 4.00 | 4.00 | 4.00 | 4.00 | 4.00 | 4.00 |
| Camphor | 2.00 | 2.00 | 2.00 | 2.00 | 2.00 | 2.00 |
| Butyl acetate | 49.50 | 49.50 | 49.50 | 49.50 | 49.50 | 49.50 |
| Toluene | 20.00 | 20.00 | 20.00 | 20.00 | 20.00 | 20.00 |
| Pigment Red 57.1 | 1.00 | 1.00 | 1.00 | 1.00 | 1.00 | 1.00 |
| Quaternary bentonite | 1.00 | 1.00 | 1.00 | 1.00 | 1.00 | 1.00 |
| stabilizer (A$_1$), (A$_2$) or (A$_3$) | 0.05 | 0.05 | 0.05 | 0.05 | 0.05 | 0.05 |
| Organic UV filter (B$_1$) | 0.02 |  |  |  |  |  |
| Organic UV filter (B$_2$) |  | 0.02 |  |  |  |  |
| Organic UV filter (B$_3$) |  |  | 0.02 |  |  |  |
| Organic UV filter (B$_4$) |  |  |  | 0.02 |  |  |
| Organic UV filter (B$_5$) |  |  |  |  | 0.02 |  |
| Organic UV filter (B$_6$) |  |  |  |  |  | 0.02 |
| Antioxidant of formula (103) | 0.10 | 0.10 | 0.10 | 0.10 | 0.10 | 0.10 |

What is claimed is:

1. A stabilized composition comprising (a) lipstick, rouge, eyeshadow or mascara, (b) from about 5 to about 10000 ppm based on the total formulation of a least one compound of formulae A*

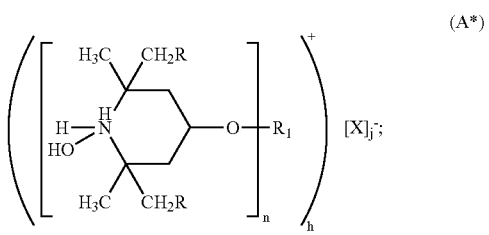

wherein
R is hydrogen or methyl,
in formula A*,
n is 1 or 2,
when n is 1,
$R_1$ is hydrogen, alkyl of 1 to 18 carbon atoms, alkenyl of 2-18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or
$R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N$^{n+}$(R$_2$)$_4$ where $R_2$ is alkyl of 1 to 8 carbon atoms or benzyl,
when n is 2,
$R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups,
X is an inorganic or organic anion, selected from the group consisting of phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and
where the total charge of cations h is equal to the total charge of anions j; and (c) an organic UV filter selected from (c$_1$) dibenzoylmethane derives.

2. A composition according to claim 1
wherein
R is hydrogen,
n is 1 or 2,
when n is 1,
$R_1$ is hydrogen, alkyl of 1 to 6 carbon atoms, alkenyl of 2 to 6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or
$R_1$ is alkyl of 1 to 4 carbon atoms substituted by a carboxy group or by —COOZ where Z is hydrogen or alkyl of 1 to 4 carbon atoms,
when n is 2,
$R_1$ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups 3. A composition according to claim 2
wherein
R is hydrogen,
h is 1,
$R_1$ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or
$R_1$ is alkyl of 1 to 4 carbon atoms substituted by -COOZ where Z is hydrogen or alkyl of 1 to 4 carbon atoms.

4. A composition according to claim 1 wherein the compounds of component (b) are selected from the group consisting of 1-hydroxy-2,2,6,6-tetramethyl-4-methoxy-piperidinium acetate; 1-hydroxy-2,2,6,6-tetramethyl-4-propoxy-piperidinium acetate; 1-hydroxy-2,2,6,6-tetramethyl-4-(2-hydroxy-4-oxapentoxy)piperidinium acetate; 1-hydroxy -2,2,6,6-tetramethyl-4-hydroxypiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium) citrate; tetra(1-hydroxy-2,2,6,6-tetramethyl-4-hydroxypiperidinium) ethylenediaminetetraacetate; penta (1-hydroxy-2,2,6,6-tetramethyl-4-hydroxypiperidinium) diethylenetriaminepentaacetate; tri(1-hydroxy-2,2,6,6-tetramethyl-4-hydroxypiperidinium) nitrilotriacetate; and penta (1-hydroxy-2,2,6,6-tetramethyl-4-hydroxypiperidinium) diethylenetriaminepentamethylenephosphonate.

5. A composition according to claim 1 wherein the compounds of component (b) are selected from the group consisting of 1-hydroxy-2,2,6,6-tetramethyl-4-hydroxypiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy -2,2,6,6-tetramethyl-4-hydroxypiperidinium) citrate; tris(1-hydroxy-2,2,6,6-tetramethyl-4-hydroxypiperidinium) citrate; tetra(1-hydroxy-2,2,6,6-tetramethyl -4-hydroxypiperidinium) ethylenediaminetetraacetate; and penta (1-hydroxy-2,2,6,6-tetramethyl-4-hydroxy-piperidinium) diethylenetriaminepentaacetate.

6. A composition according to claim 1 in which the compounds of component (b) are selected from the group consisting of 1-hydroxy-2,2,6,6-tetramethyl-4-hydroxypiperidinium citrate; bis(1-hydroxy-2,2,6,6-tetramethyl-4-hydroxypiperidinium) citrate; tris(1-hydroxy-2,2,6,6-tetramethyl-4-hydroxypiperidinium) citrate; 1-hydroxy-2,2,6,6-tetramethyl-4-hydroxypiperidinium DTPA; bis(1-hydroxy-2,2,6,6-tetramethyl-4-hydroxypiperidinium) DTPA; tris(1-hydroxy-2,2,6,6-tetramethyl-4-hydroxypiperidinium) DTPA; tetrakis(1-hydroxy-2,2,6,6-tetramethyl-4-hydroxypiperidinium) DTPA; pentakis(1-hydroxy-2,2,6,6-tetramethyl-4-hydroxypiperidinium) DTPA; 1 -hydroxy-2,2,6,6-tetramethyl -4-hydroxypiperidinium EDTA; bis(1-hydroxy-2,2,6,6-tetramethyl-4-hydroxypiperidinium)

EDTA; tris(1-hydroxy-2,2,6,6-tetramethyl-4-hydroxypiperidinium) EDTA; tetrakis(1-hydroxy-2,2,6,6-tetramethyl-4-hydroxypiperidinium) EDTA; and tetrakis(1-hydroxy-2,2,6,6-tetramethyl-4-hydroxypiperidinium) EDTA.

7. A composition according to claim 1, wherein ($c_1$) is selected from Butyl Methoxydibenzoylmethane, Ethylhexyl Methoxydibenzoylmethane and Isopropyl Dibenzoylmethane 8. A composition according to claim 7, wherein ($c_1$) is 1-(4-tert-butylphenyl)-3-(4-methoxyphenyl)propane-1,3-dione.

9. A composition according to claim 1 further comprising
(d) at least one compound selected from the group consisting of antioxidants, tocopherol, tocopherol acetate, hindered amine light stabilizers, complex formers, optical brighteners, surfactants, and polyorganosiloxanes.

10. A composition according to claim 1 wherein the ratio of component (b) to component (c) is from 1:1000 to 1000:1.

* * * * *